(12) United States Patent
Rasmussen

(10) Patent No.: US 8,969,300 B2
(45) Date of Patent: Mar. 3, 2015

(54) NA-K PUMP MODULATION

(76) Inventor: Helge H. Rasmussen, Neutral Bay (AU)

( * ) Notice: Subject to any disclaimer, the term of this patent is extended or adjusted under 35 U.S.C. 154(b) by 0 days.

(21) Appl. No.: 13/501,394

(22) PCT Filed: Oct. 15, 2010

(86) PCT No.: PCT/AU2010/001367
§ 371 (c)(1),
(2), (4) Date: Jul. 25, 2012

(87) PCT Pub. No.: WO2011/044636
PCT Pub. Date: Apr. 21, 2011

(65) Prior Publication Data
US 2012/0283189 A1    Nov. 8, 2012

(30) Foreign Application Priority Data

Oct. 15, 2009  (AU) .................................. 2009905055

(51) Int. Cl.
| | | |
|---|---|---|
| *A61K 38/00* | (2006.01) | |
| *A61P 39/06* | (2006.01) | |
| *A61P 35/00* | (2006.01) | |
| *C07K 14/47* | (2006.01) | |

(52) U.S. Cl.
CPC ............. *C07K 14/4702* (2013.01); *A61K 38/00* (2013.01)
USPC ........ 514/15.1; 514/19.3; 514/19.4; 514/19.5

(58) Field of Classification Search
CPC ............................. C07K 14/4702; A61K 38/00
See application file for complete search history.

(56) References Cited

U.S. PATENT DOCUMENTS

2010/0154071 A1\*  6/2010  Fanidi et al. ..................... 800/13

FOREIGN PATENT DOCUMENTS

| AU | 2010306414 | 5/2012 |
|---|---|---|
| CA | 2777250 | 4/2011 |
| EP | 2488256 | 8/2012 |
| WO | 2011/044636 | 4/2011 |

OTHER PUBLICATIONS

Figtree G "Protecting the heart from ischemia-reperfusion injury: A new role for FXYD proteins?" Published Mar. 31, 2009. Retrieved on Oct. 18, 2012 from the Internet. <URL: http://sydney.edu.au/research/opportunities/opportunities/1424 >.\*
Zhu et al "Expression and significance of FXYD-3 protein in gastric adenocarcinoma" Disease Markers 28:63-69. Published Apr. 2, 2010.\*
Maxwell, Pamela J., et al., "Identification of 5-fluorouracil-inducible Target Genes Using cDNA Microarray Profiling," Cancer Research, 63 Aug. 1, 2003, pp. 4602-4606.
Loftas, Per, M.D., et al., "Expression of FXYD-3 is an Independent Prognostic Factor in Rectal Cancer Patients With Preoperative Radiotherapy," Int. J. Radiation Oncology Biol. Phys., vol. 75,No. 1, pp. 137-142 (2009).
Miller, Timothy J., et al., "FXYD5 modulates Na+ absorption and is increased in cystic fibrosis airway epithelia," Am J. Physiol. Lung Cell Mol. Physiol. 294: L654-L664 (2008).
Okudela, Koji, et al., "Down-Regulation of FXYD3 Expression in Human Lung Cancers," The American Journal of Pathology, vol. 175, No. 6, Dec. 2009, pp. 2646-2655.
Geering, Kathi, "FXYD proteins: new regulators of Na-K-ATPase," Am. J. Physiol Renal Physiol 290: F241-F250 (2006).
Lubarski, Irina, et al., "Structural and functional interactions between FXYD5 and the Na+-K+-ATPase," Am J Physiol Renal Physiol 293: F1818-F1826 (2007).
Lubarski, Irina, et al., Interaction with the Na,K-ATPase and Tissue Districbution of FXYD5 (Related to Ion Channel), The Journal of Biological Chemistry, vol. 280, No. 45, pp. 37717-37724, Nov. 11, 2005.
Yamaguchi, F. et al, "Molecular cloning and characterization of a novel phospholemman-like protein from rat hippocampus", (2001) Molecular Brain Research, vol. 86, pp. 189-192.
Arimochi, J. et al, "Interaction of Mat-8 (FXYD-3) with Na+/K+-ATPase in Colorectal Cancer Cells", (2007) Biol. Pharm. Bull. 30(4), 648-654.
Attali, B. et al, "A corticosteroid-induced gene expressing an "IsK-like" K+ channel activity in *Xenopus* oocytes(ion channels/phospholemman/Na+,K+-ATPase/epithelial transport/aldosterone)" (1995) Proceedings of the National Acadamy of Science of the United States of America, vol. 92, pp. 6092-6096.
Béguin, P. et al, "FXYD7 is a brain-specific regulator of Na,K-ATPase α1-β isozymes" (2002), The EMBO Journal vol. 21(13) pp. 3264-3273.
Bundgaard, H., et al, "β3 Adrenergic Stimulation of the Cardiac Na+-K+ Pump by Reversal of an Inhibitory Oxidative Modification" (2010), Circulation—Journal of the American Heart Association, vol. 122, pp. 2699-2708.
Chow, D.C., et al, "Gastric H+-K+-ATPase activity is inhibited by reduction of disulfide bonds in β-subunit", (1992), American Journal of Physiology—Cell Physiology, vol. 263, pp. C39-C46.
Cornelius, F. and Mahmmound, Y. A., "Functional Modulation of the Sodium Pump: The Regulatory Proteins "Fixit"" (2003), News Physiol Sci, vol. 18, pp. 119-124.
Crowell, K J., et al, "Expression and characterization of the FXYD ion transport regulators for NMR structural studies in lipid micelles and lipid bilayers" (2003), Biochim Biophys Acta, vol. 1645(1), pp. 15-21.
Deng, V., et al, "FXYD1 is an MeCP2 target gene overexpressed in the brains of Rett syndrome patients and Mecp2-null mice" (2007), Human Molecular Genetics, vol. 16(6), pp. 640-650.

(Continued)

*Primary Examiner* — James H Alstrum Acevedo
*Assistant Examiner* — Zachary J Miknis
(74) *Attorney, Agent, or Firm* — Casimir Jones S.C.

(57) ABSTRACT

The present invention relates to a method of modulating $Na^+/K^+$ pump activity, the method comprising contacting the $Na^+/K^+$ pump with an FXYD protein or a fragment or variant thereof wherein glutathionylation of said $Na^+/K^+$ pump is altered by said FXYD protein.

8 Claims, 10 Drawing Sheets

(56) References Cited

OTHER PUBLICATIONS

Figtree, G.A., et al, "Reversible Oxidative Modification—A Key Mechanism of Na+-K+ Pump Regulation", (2009), Circulation Research, vol. 105, pp. 185-193.
Figtree, G., "Protecting the heart from ischemia-reperfusion injury: A new role for FXYD proteins?" Retreived on Oct. 18, 2012 from the Internet. <URL: http://sydney.edu.au/research/opportunities/opportunities/1424>.
Fu, X. and Kamps, M. P., "E2a-Pbx1 Induces Aberrant Expression of Tissue-Specific and Developmentally Regulated Genes When Expressed in NIH 3T3 Fibroblasts" (1997), Molecular and Cellular Biology, vol. 17(3), pp. 1503-1512.
Garcia, A., et al, "β3 adrenergic stimulation of the Na+-K+ pump is mediated by NO-dependent deglutathionylation of the β1 pump subunit" (2008), Proceedings from the 12th International ATPase Conference, Aarhus, Denmark (abstract).
Garty, H. and Karlish, S. J. D., "Role of FXYD Proteins in Ion Transport" (2006) Annual Review of Physiology, vol. 68 pp. 431-459.
Geering, K., "FXYD proteins: new regulators of Na-K-ATPase" (2006), American Journal of Physiology—Renal Physiology, vol. 290, pp. F241-F250.
Geering, K., "The functional role of the β-subunit in the maturation and intracellular transport of Na, K-ATPase", (1991), Federation of European Biochemical Societies, vol. 285(2), pp. 189-193.
Ghezzi, P., "Regulation of protein function by glutathionylation" (2005), Free Radical Research, vol. 39(6), pp. 573-580.
Kayed, H., et al, "FXYD3 is overexpressed in pancreatic ductal adenocarcinoma and influences pancreatic cancer cell growth", (2006), International Journal of Cancer, vol. 118, pp. 43-54.
White, C.N., et al, "Angiotensin II inhibits the Na+-K+ pump via PKC-dependent activation of NADPH oxidase" (2009), American Journal of Physiology—Cell Physiology, vol. 296, pp. C693-C700.
Lubarski, I. et al, Interaction with the Na, K-ATPase and Tissue Distribution of FXYD5 (Related to Ion Channel) (2005), The Journal of Biological Chemistry, vol. 280(45), pp. 37717-37724.
Lubarski, I. et al, "Structural and functional interactions between FXYD5 and the Na+-K+-ATPase" (2007), American Journal of Physiology—Renal Physiology, vol. 293, pp. F1818-F1826.
White, C.N., et al, "Activation of cAMP-dependent Signaling Induces Oxidative Modification of the Cardiac Na+-K+ Pump and Inhibits Its Activity", (2010), The Journal of Biological Chemistry, vol. 285(18), pp. 13712-13720.
Mercer, R.W., et al, "Molecular Cloning and Immunological Characterization of the γ Polypeptide, a Small Protein Associated with the Na,K-ATPase" (1993), The Journal of Cell Biology, vol. 121(3), pp. 579-586.
Meij, I.C., et al, "Dominant isolated renal magnesium loss is caused by misrouting of the Na+,K+-ATPase γ-subunit", (2000), Nature Genetics, vol. 26, pp. 265-266.
Mijatovic, T., et al, "Cardiotonic steroids on the road to anti-cancer therapy" (2007), Biochimica et Biophysica Acta vol. 1776, pp. 32-57.
Mijatovic, T. et al, "Na + /K + -ATPase a subunits as new targets in anticancer therapy" (2008), Expert Opinion on Therapeutic Targets, vol. 12(11) pp. 1403-1417.
Wetzel, R. K., "Stress-induced Expression of the _ Subunit (FXYD2) Modulates Na,K-ATPase Activity and Cell Growth" (2004), The Journal of Biological Chemistry vol. 279(40), pp. 41750-41757.
Morrison, B.W., et al, "Mat-8, a Novel Phospholemman-like Protein Expressed in Human Breast Tumors, Induces a Chloride Conductance in *Xenopus* Oocytes" (1995), The Journal of Biological Chemistry, vol. 270(5), pp. 2176-2182.
Morth, J.P., et al, "Crystal structure of the sodium-potassium pump" (2007), Nature Publishing Group, vol. 450(13), pp. 1043-1050.
Nam, J.-S., et al, "Chemokine (C-C Motif) Ligand 2 Mediates the Prometastatic Effect of Dysadherin in Human Breast Cancer Cells" (2006), Cancer Research, vol. 66, pp. 7176-7184.
Wang, J. K. T., et al, "Cardiac glycosides provide neuroprotection against ischemic stroke: Discovery by a brain slice-based compound screening platform" (2006) vol. 103(27), pp. 10461-10466.
Palmer, C.J., et al, "Purification and Complete Sequence Determination of the Major Plasma Membrane Substrate for cAMP-dependent Protein Kinase and Protein Kinase C in Myocardium" (1991), The Journal of Biological Chemistry, vol. 266(17), pp. 11126-11130.
Pierre, S. V. et al, "Ouabain triggers preconditioning through activation of the Na+,K+-ATPase signaling cascade in rat hearts" (2007) Cardiovascular Research vol. 73 pp. 488-496.
Presti, C.F., et al, "Isoproterenol-induced Phosphyorylation of a 15-Kilodalton Sarcolemmal Protein in Intact Myocardium" (1985), The Journal of Biological Chemistry, vol. 260(6), pp. 3860-3867.
Shattock, M. J., "Phospholemman: its role in normal cardiac physiology and potential as a drugable target in disease" (2009) Current Opinion in Pharmacology, vol. 9(2) pp. 160-166.
Shinoda, T., et al, "Crystal structure of the sodium-potassium pump at 2.4Å resolution" (2009), Nature, vol. 459, pp. 446-451.
Sweadner, K.J., et al, "The FXYD Gene Family of Small Ion Transport Regulators or Channels: cDNA Sequence, Protein Signature Sequence, and Expression", (2000), Genomics vol. 68, pp. 41-56.
Nakanishi Y., et al, "Prognostic significance of dysadherin expression in tongue cancer: Immunohistochemical analysis of 91 cases" (2004), Applied Immunohistochemistry & Molecular Morphology, vol. 12, No. 4, pp. 323-328.
Wong, J. C. et al., "W1877 Changes in FXYD3 and NPM1 Expressions are Early Markers of Adenomas in the Colon" (2009) Gastroenterology, vol. 136(5) pp. A-745.
George, Susan R., et al., "A Transmembrane Domain-derived Peptide Inhibits D1 Dopamine Receptor Function without Affecting Receptor Oligomerization," The Journal of Biological Chemistry, vol. 273, No. 46, Issue of Nov. 13, pp. 30244-30248 (1998).
George, Susan R., et al., "Blockade of G Protein-Coupled Receptors and the Dopamine Transporter by a Transmembrane Domain Peptide: Novel Strategy for Functional Inhibition of Membrane Proteins in Vivo," The Journal of Pharmacology and Experimental Therapeutics, vol. 307, No. 2 (2003), pp. 481-489.
Manolios, Nicholas, et al., "T-cell receptor (TCR) transmembrane peptides," Cell Adhesion & Migration 4-2, 273-283 (2010).
Hubert, Pierre, et al., "Single-spanning transmembrane domains in cell growth and cell-cell interactions," Cell Adhesion & Migration (2010), pp. 313-324.
Franzin, Carla M., et al., "Correlation of Gene and Protein Structures in the FXYD Family Proteins," J Mol Biol. Dec. 9, 2005; 354(4): 743-750.
Teriete, Peter, et al., "Structure of the Na,K-ATPase regulatory protein FXYD1 in micelles," Biochemistry Jun. 12, 2007; 46(23); 6774-6783.
Morth, J. Preben, et al., "Crystal structure of the sodium-potassium pump", Nature, vol. 450, Dec. 13, 2007, p. 1043.
Shinoda, Takehiro, et al., "Crystal structure of the sodium-potassium pump at 2.4 A resolution," Nature, vol. 459, May 21, 2009, p. 446.
Nasarre, C., et al., "Peptide-based interference of the transmembrane domain of neuropilin-1 inhibits glioma growth in vivo," Oncogene (2010) 29, 2381-2392.
Grzmil, Michal, et al., "Up-regulated expression of the MAT-9 gene in prostate cancer and its siRNA-mediated inhibition of expression induces a decrease in proliferation of human prostate carcinoma cells," International Journal of Oncology 24: 97-105 (2004).
Kayed, Hany, et al., "FXYD3 is overexpressed in pancreatic ductal adenocarcinoma and influences pancreatic cancer cell growth," Int. J. Cancer: 118, 43-54 (2006).
Bibert, Stephanie, et al., "A Link between FXYD3 (Mat-8)-mediated Na,K-ATPase Regulation and Differentiation of Caco-2 Intestinal Epithelial Cells," Molecular Biology of the Cell, vol. 20 1132-1140, Feb. 15, 2009.
Loftas, Per, et al,. "Expression of FXYD-3 is an Independent Prognostic Factor in Rectal Cancer Patients with Preoperative Radiotherapy," Int. J. Radiation Oncology Biol. Phys. vol. 75, No. 1, pp. 137-142 (2009).

\* cited by examiner

| | | | | |
|---|---|---|---|---|
| FXYD1 (SEQ ID NO 15) | 51 | GILIVLSRR...EGTFRSSIRRLSTRRR | 92 |
| FXYD2 (SEQ ID NO 16) | 41 | GLLILLSRR...KRRQIMEDEP | 66 |
| FXYD3 (SEQ ID NO 17) | 52 | GIIYVMSAR...PLITPGSAQS | 87 |
| FXYD4 (SEQ ID NO 18) | 52 | GIAAVLSGR...PLITPGSATTC | 89 |
| FXYD5 (SEQ ID NO 19) | 157 | GILILTSGR...QLSRLCRNRCR | 178 |
| FXYD6 (SEQ ID NO 20) | 52 | GILLILSRR...AQVENLITANATEPQKAEN | 95 |
| FXYD7 (SEQ ID NO 21) | 40 | GILIVISKR...CKSEPSSAPGGGV | 79 |

SEQUENCE LISTING

```
<160> NUMBER OF SEQ ID NOS: 21

<210> SEQ ID NO 1
<211> LENGTH: 92
<212> TYPE: PRT
<213> ORGANISM: Homo sapiens

<400> SEQUENCE: 1

Met Ala Ser Leu Gly His Ile Leu Val Phe Cys Val Gly Leu Leu Thr
1               5                   10                  15

Met Ala Lys Ala Glu Ser Pro Lys Glu His Asp Pro Phe Thr Tyr Asp
            20                  25                  30

Tyr Gln Ser Leu Gln Ile Gly Gly Leu Val Ile Ala Gly Ile Leu Phe
        35                  40                  45

Ile Leu Gly Ile Leu Ile Val Leu Ser Arg Arg Cys Arg Cys Lys Phe
    50                  55                  60

Asn Gln Gln Gln Arg Thr Gly Glu Pro Asp Glu Glu Glu Gly Thr Phe
65                  70                  75                  80

Arg Ser Ser Ile Arg Arg Leu Ser Thr Arg Arg Arg
                85                  90

<210> SEQ ID NO 2
<211> LENGTH: 66
<212> TYPE: PRT
<213> ORGANISM: Homo sapiens

<400> SEQUENCE: 2

Met Thr Gly Leu Ser Met Asp Gly Gly Gly Ser Pro Lys Gly Asp Val
1               5                   10                  15

Asp Pro Phe Tyr Tyr Asp Tyr Glu Thr Val Arg Asn Gly Gly Leu Ile
            20                  25                  30

Phe Ala Gly Leu Ala Phe Ile Val Gly Leu Leu Ile Leu Leu Ser Arg
        35                  40                  45

Arg Phe Arg Cys Gly Gly Asn Lys Lys Arg Arg Gln Ile Asn Glu Asp
    50                  55                  60

Glu Pro
65
```

-continued

```
<210> SEQ ID NO 3
<211> LENGTH: 87
<212> TYPE: PRT
<213> ORGANISM: Homo sapiens

<400> SEQUENCE: 3

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
                20                  25                  30

Asp Trp His Ser Leu Gln Val Gly Gly Leu Ile Cys Ala Gly Val Leu
            35                  40                  45

Cys Ala Met Gly Ile Ile Ile Val Met Ser Ala Lys Cys Lys Cys Lys
        50                  55                  60

Phe Gly Gln Lys Ser Gly His His Pro Gly Glu Thr Pro Pro Leu Ile
65                  70                  75                  80

Thr Pro Gly Ser Ala Gln Ser
                85

<210> SEQ ID NO 4
<211> LENGTH: 89
<212> TYPE: PRT
<213> ORGANISM: Homo sapiens

<400> SEQUENCE: 4

Met Glu Arg Val Thr Leu Ala Leu Leu Leu Ala Gly Leu Thr Ala
1               5                   10                  15

Leu Glu Ala Asn Asp Pro Phe Ala Asn Lys Asp Pro Phe Tyr Tyr
                20                  25                  30

Asp Trp Lys Asn Leu Gln Leu Ser Gly Leu Ile Cys Gly Gly Leu Leu
            35                  40                  45

Ala Ile Ala Gly Ile Ala Ala Val Leu Ser Gly Lys Cys Lys Cys Lys
        50                  55                  60

Ser Ser Gln Lys Gln His Ser Pro Val Pro Glu Lys Ala Ile Pro Leu
65                  70                  75                  80

Ile Thr Pro Gly Ser Ala Thr Thr Cys
                85

<210> SEQ ID NO 5
<211> LENGTH: 178
<212> TYPE: PRT
<213> ORGANISM: Homo sapiens

<400> SEQUENCE: 5

Met Ser Pro Ser Gly Arg Leu Cys Leu Leu Thr Ile Val Gly Leu Ile
1               5                   10                  15

Leu Pro Thr Arg Gly Gln Thr Leu Lys Asp Thr Thr Ser Ser Ser Ser
                20                  25                  30

Ala Asp Ser Thr Ile Met Asp Ile Gln Val Pro Thr Arg Ala Pro Asp
            35                  40                  45

Ala Val Tyr Thr Glu Leu Gln Pro Thr Ser Pro Thr Pro Thr Trp Pro
        50                  55                  60

Ala Asp Glu Thr Pro Gln Pro Gln Thr Gln Thr Gln Leu Glu Gly
65                  70                  75                  80

Thr Asp Gly Pro Leu Val Thr Asp Pro Glu Thr His Lys Ser Thr Lys
                85                  90                  95

Ala Ala His Pro Thr Asp Asp Thr Thr Thr Leu Ser Glu Arg Pro Ser
            100                 105                 110
```

Pro Ser Thr Asp Val Gln Thr Asp Pro Gln Thr Leu Lys Pro Ser Gly
            115                 120                 125

Phe His Glu Asp Pro Phe Phe Tyr Asp Glu His Thr Leu Arg Lys
    130                 135                 140

Arg Gly Leu Leu Val Ala Ala Val Leu Phe Ile Thr Gly Ile Ile Ile
145                 150                 155                 160

Leu Thr Ser Gly Lys Cys Arg Gln Leu Ser Arg Leu Cys Arg Asn Arg
                165                 170                 175

Cys Arg

<210> SEQ ID NO 6
<211> LENGTH: 95
<212> TYPE: PRT
<213> ORGANISM: Homo sapiens

<400> SEQUENCE: 6

Met Glu Leu Val Leu Val Phe Leu Cys Ser Leu Leu Ala Pro Met Val
1               5                   10                  15

Leu Ala Ser Ala Ala Glu Lys Glu Lys Glu Met Asp Pro Phe His Tyr
            20                  25                  30

Asp Tyr Gln Thr Leu Arg Ile Gly Gly Leu Val Phe Ala Val Val Leu
        35                  40                  45

Phe Ser Val Gly Ile Leu Leu Ile Leu Ser Arg Arg Cys Lys Cys Ser
    50                  55                  60

Phe Asn Gln Lys Pro Arg Ala Pro Gly Asp Glu Glu Ala Gln Val Glu
65                  70                  75                  80

Asn Leu Ile Thr Ala Asn Ala Thr Glu Pro Gln Lys Ala Glu Asn
                85                  90                  95

<210> SEQ ID NO 7
<211> LENGTH: 79
<212> TYPE: PRT
<213> ORGANISM: Homo sapiens

<400> SEQUENCE: 7

Met Ala Thr Pro Thr Gln Thr Pro Thr Lys Ala Pro Glu Glu Pro Asp
1               5                   10                  15

Pro Phe Tyr Tyr Asp Tyr Asn Thr Val Gln Thr Val Gly Met Thr Leu
            20                  25                  30

Ala Thr Ile Leu Phe Leu Leu Gly Ile Leu Ile Val Ile Ser Lys Lys
        35                  40                  45

Val Lys Cys Arg Lys Ala Asp Ser Arg Ser Glu Ser Pro Thr Cys Lys
    50                  55                  60

Ser Cys Lys Ser Glu Pro Ser Ser Ala Pro Gly Gly Gly Gly Val
65                  70                  75

<210> SEQ ID NO 8
<211> LENGTH: 279
<212> TYPE: DNA
<213> ORGANISM: Homo sapiens

<400> SEQUENCE: 8
atggcacctc tccaccacat cttggttttc tgtgtgggtc tcctcaccat ggccaaggca      60
gaaagtccaa aggaacacga cccgttcact tacgactacc agtccctgca gatcggaggc     120
ctcgtcatcg ccgggatcct cttcatcctg ggcatcctca tcgtgctgag cagaagatgc     180

```
cggtgcaagt tcaaccagca gcagaggact ggggaacccg atgaagagga gggaactttc      240
cgcagctcca tccgccgtct gtccacccgc aggcggtag                              279

<210> SEQ ID NO 9
<211> LENGTH: 177
<212> TYPE: DNA
<213> ORGANISM: Homo sapiens

<400> SEQUENCE: 9
gtggcggcag ccaaggggga cgtggacccg ttctactatg actatgagac cgttcgcaat       60
gggggcctga tcttcgctgg actggccttc atcgtggggc tcctcatcct cctcagcaga      120
agattccgct gtgggggcaa taagaagcgc aggcaaatca tgaagatga gccgtaa          177

<210> SEQ ID NO 10
<211> LENGTH: 261
<212> TYPE: DNA
<213> ORGANISM: Homo sapiens

<400> SEQUENCE: 10
atgcagaagg tgaccctggg cctgcttgtg ttcctggcag gctttcctgt cctggacgcc       60
aatgacctag aagataaaaa cagtcctttc tactatgact ggcacagcct ccaggttggc      120
gggctcatct gcgctggggt tctgtgcgcc atgggcatca tcatcgtcat gagtgcaaaa      180
tgcaaatgca gtttggcca gaagtccggt caccatccag gggagactcc acctctcatc       240 accccggct cagcccaaag c                                                  261

<210> SEQ ID NO 11
<211> LENGTH: 270
<212> TYPE: DNA
<213> ORGANISM: Homo sapiens

<400> SEQUENCE: 11
atggagagag tgaccctggc ccttctccta ctggcaggcc tgactgcctt ggaagccaat       60
gacccatttg ccaataaaga cgatcccttc tactatgact ggaaaaacct gcagctgagc      120
ggactgatct gcgagggct cctggccatt gctgggatcg cggcagttct gagtggcaaa       180
tgcaaatgca agagcagcca gaagcagcac agtcctgtac ctgagaaggc catcccactc      240
atcactccag gctctgccac tacttgctga                                        270

<210> SEQ ID NO 12
<211> LENGTH: 477
<212> TYPE: DNA
<213> ORGANISM: Homo sapiens

<400> SEQUENCE: 12
ggacagacgt tgaaagatac cacgtccagt tcttcagcag actcaactat catggacatt       60
caggtcccga cacgagcccc agatgcagtc tacacagaac tccagcccac ctctccaacc      120
ccaacctggc ctgctgatga acaccacaa ccccagaccc agaccca gca actggaagga      180 acggatgggc tctagtgac agatccgag acacacaaga gcaccaaagc agctcatccc       240
actgatgaca ccacgacgct ctctgagaga ccatccccaa gcacagacgt ccagacagac      300
ccccagaccc tcaagccatc tggttttcat gaggatgacc ccttcttcta tgatgaacac      360
accctccgga acggggggct gttggtcgca gctgtgctgt tcatcacagg catcatcatc      420
ctcaccagtg gcaagtgcag gcagctgtcc cggttatgcc ggaatcgttg caggtga        477
```

<210> SEQ ID NO 13
<211> LENGTH: 288
<212> TYPE: DNA
<213> ORGANISM: Homo sapiens

<400> SEQUENCE: 13
atggagttgg tgctggtctt cctctgcagc ctgctggccc ccatggtcct ggccagtgca    60
gctgaaaagg agaaggaaat ggaccctttt cattatgatt accagaccct gaggattggg   120
ggactggtgt tcgctgtggt cctcttctcg gttgggatcc tccttatcct aagtcgcagg   180
tgcaagtgca gtttcaatca gaagcccngg gccccaggag atgaggaagc ccaggtggag   240
aacctcatca ccgccaatgc aacagagccc cagaaagcag agaactga              288

<210> SEQ ID NO 14
<211> LENGTH: 243
<212> TYPE: DNA
<213> ORGANISM: Homo sapiens

<400> SEQUENCE: 14
atggcgaccc cgacccagac ccccacaaag gctcctgagg aacctgaccc attttactat    60
gactacaaca cggtgcagac tgtgggcatg actctggcaa ccatcttgtt cctgctgggt   120
atcctcatcg tcatcagcaa gaaggtgaag tgcaggaagg cggactccag gtctgagagc   180
ccaacctgca atcctgtaa gtctgagctt ccctcttcag cccctggtgg cggcggcgtg   240
taa                                                                243

<210> SEQ ID NO 15
<211> LENGTH: 42
<212> TYPE: PRT
<213> ORGANISM: Homo sapiens

<400> SEQUENCE: 15

Gly Ile Leu Ile Val Leu Ser Arg Arg Cys Arg Cys Lys Phe Asn Gln
1               5                   10                  15

Gln Gln Arg Thr Gly Glu Pro Asp Glu Glu Glu Gly Thr Phe Arg Ser
            20                  25                  30

Ser Ile Arg Arg Leu Ser Thr Arg Arg Arg
        35                  40

<210> SEQ ID NO 16
<211> LENGTH: 26
<212> TYPE: PRT
<213> ORGANISM: Homo sapiens

<400> SEQUENCE: 16

Gly Leu Leu Ile Leu Leu Ser Arg Arg Phe Arg Cys Gly Gly Asn Lys
1               5                   10                  15

Lys Arg Arg Gln Ile Asn Glu Asp Glu Pro
            20                  25

<210> SEQ ID NO 17
<211> LENGTH: 36
<212> TYPE: PRT
<213> ORGANISM: Homo sapiens

<400> SEQUENCE: 17

Gly Ile Ile Ile Val Met Ser Ala Lys Cys Lys Cys Lys Phe Gly Gln
1               5                   10                  15

```
Lys Ser Gly His His Pro Gly Glu Thr Pro Pro Leu Ile Thr Pro Gly
            20                  25                  30

Ser Ala Gln Ser
        35
```

<210> SEQ ID NO 18
<211> LENGTH: 38
<212> TYPE: PRT
<213> ORGANISM: Homo sapiens

<400> SEQUENCE: 18

```
Gly Ile Ala Ala Val Leu Ser Gly Lys Cys Lys Cys Lys Ser Ser Gln
1               5                   10                  15

Lys Gln His Ser Pro Val Pro Glu Lys Ala Ile Pro Leu Ile Thr Pro
            20                  25                  30

Gly Ser Ala Thr Thr Cys
        35
```

<210> SEQ ID NO 19
<211> LENGTH: 22
<212> TYPE: PRT
<213> ORGANISM: Homo sapiens

<400> SEQUENCE: 19

```
Gly Ile Ile Ile Leu Thr Ser Gly Lys Cys Arg Gln Leu Ser Arg Leu
1               5                   10                  15

Cys Arg Asn Arg Cys Arg
            20
```

<210> SEQ ID NO 20
<211> LENGTH: 44
<212> TYPE: PRT
<213> ORGANISM: Homo sapiens

<400> SEQUENCE: 20

```
Gly Ile Leu Leu Ile Leu Ser Arg Arg Cys Lys Cys Ser Phe Asn Gln
1               5                   10                  15

Lys Pro Arg Ala Pro Gly Asp Glu Glu Ala Gln Val Glu Asn Leu Ile
            20                  25                  30

Thr Ala Asn Ala Thr Glu Pro Gln Lys Ala Glu Asn
        35                  40
```

<210> SEQ ID NO 21
<211> LENGTH: 40
<212> TYPE: PRT
<213> ORGANISM: Homo sapiens

<400> SEQUENCE: 21

```
Gly Ile Leu Ile Val Ile Ser Lys Lys Val Lys Cys Arg Lys Ala Asp
1               5                   10                  15

Ser Arg Ser Glu Ser Pro Thr Cys Lys Ser Cys Lys Ser Glu Pro Ser
            20                  25                  30

Ser Ala Pro Gly Gly Gly Gly Val
        35                  40
```

.# NA-K PUMP MODULATION

CROSS-REFERENCE TO RELATED APPLICATIONS

This application is a U.S. 371 national stage entry of pending International (PCT) Patent Application No. PCT/AU2010/001367, international filing date Oct. 15, 2010, which claims the benefit of Australian Provisional Patent Application No. AU2009905055, filed Oct. 15, 2009, the contents of each of which are hereby incorporated by reference for all purposes.

TECHNICAL FIELD

The present invention relates to the modulation of oxidative inhibition of $Na^+$—$K^+$ pump activity. In particular the present invention relates to the modulation of oxidative inhibition of $Na^+$—$K^+$ pump activity by FXYD proteins. The present invention also relates to FXYD proteins and derivatives thereof useful in the treatment of mammals, particularly humans, having conditions involving oxidative inhibition of the $Na^+$—$K^+$ pump.

BACKGROUND

FXYD proteins 1-7 are a family of single transmembrane-spanning proteins that are named after their shared FXYD amino acid motif in the extracellular domain. FXYD proteins are known for an effect they are believed to have on membrane proteins they associate with, in particular the membrane $Na^+$—$K^+$ ATPase. FXYD proteins do not form part of $Na^+$—$K^+$ pump per se but act as tissue specific modulators of $Na^+$—$K^+$ pump function.

FXYD proteins have been widely implicated in regulation of $Na^+$—$K^+$ pump function, and it is known that they indeed modify functional properties of the pump. In particular FXYD1, unique among FXYD proteins in that it can be phosphorylated on C-terminal serine residues, is understood to regulate the $Na^+$—$K^+$ pump in response to phosphorylation. However, a problem with this understanding is that FXYD proteins 2-7 have no functional phosphorylation sites and most tissues do not express FXYD1, thus phosphorylation of FXYD proteins cannot be a universally applicable scheme for $Na^+$—$K^+$ pump regulation by FXYD proteins.

The transmembrane gradients for $Na^+$ and $K^+$ maintained by the $Na^+$—$K^+$ pump are critical for generation of membrane potentials and hence cell excitability. They also drive secondary co- and counter-transport processes for other ions as well as for a large number of organic compounds, critical for cell metabolism. The pump and the wider superfamily of cation-transporting ATPases it belongs to are important therapeutic targets. However, despite having been discovered over 50 years ago modulation of $Na^+$—$K^+$ pump activity remains poorly understood.

The inventors have previously illustrated a role for oxidative signalling in regulation of the $Na^+$—$K^+$ pump in that the $\beta_1$ subunit of the $Na^+$—$K^+$ pump $\alpha/\beta$ heterodimer has a "reactive" cysteine residue capable of being glutathionylated and that such glutathionylation reversibly inhibits $Na^+$—$K^+$ pump function. Glutathionylation can be induced by chemical oxidants or mediated by membrane receptor- and protein kinase-dependent activation of NADPH oxidase.

Oxidative stress is an important factor in a number of diseases including myocardial infarction, stroke and cancer. Increased oxidative stress and high levels of myocyte $Na^+$ and $Ca^+$ contribute to myocardial damage and contractile abnormalities in ischemia and reperfusion.

In response to oxidative stress, the $\beta_1$ subunit of the $Na^+$—$K^+$ pump is glutathionylated in infarction and pump inhibition caused by this may contribute to the raised $Na^+$ and $Ca^{2+}$ levels. Oxidative stress has also been implicated in cerebral ischmaemic damage with stroke, and antioxidant strategies examined. Furthermore oxidative stress is known to be an important factor in ischemia reperfusion injury.

There remains a need for improved methods for the modulation of Na/K pump activity, such as for use in therapeutic context where inhibition of pump activity is associated with detriment to health.

SUMMARY

The present invention is based on the surprising finding that FXYD proteins modulate oxidative inhibition of the $Na^+$/$K^+$ pump by altering $Na^+$/$K^+$ pump glutathionylation.

The present invention provides methods for modulating $Na^+$/$K^+$ pump activity by altering $Na^+$/$K^+$ pump glutathionylation. In preferred embodiments the present invention aims to provide methods for the treatment of myocardial infarction, stroke, cancer and ischemia reperfusion injury.

In one aspect the invention provides a method of treatment or prevention of a condition associated with excessive glutathionylation of a $Na^+$/$K^+$ pump, the method comprising contacting said pump with an effective amount of an FXYD protein.

In one aspect of the present invention there is provided an FXYD protein or fragment or variant thereof for use in a method of treatment or prevention of a condition associated with excessive glutathionylation of a $Na^+$/$K^+$ pump.

In one embodiment the condition associated with excessive glutathionylation of the Na/K pump is selected from the group consisting of myocardial infarction, stroke, cancer and ischemia reperfusion injury.

In one aspect of the present invention there is provided a method of modulating $Na^+$/$K^+$ pump activity, the method comprising contacting the $Na^+$/$K^+$ pump with an FXYD protein or a fragment or variant thereof wherein glutathionylation of said $Na^+$/$K^+$ pump is altered by said FXYD protein or fragment or variant thereof.

In one aspect of the present invention there is provided an FXYD protein or fragment or variant thereof for use in a method of modulating $Na^+$/$K^+$ pump activity.

In one aspect of the present invention there is provided a method for treating myocardial infarction, stroke, or ischemia reperfusion injury by modulating $Na^+$/$K^+$ pump activity in a subject, the method comprising administering to said individual a therapeutically effective amount of an FXYD protein or a fragment or variant thereof wherein said FXYD protein or fragment or variant thereof promotes deglutathionylation of said $Na^+$/$K^+$ pump thereby modulating $Na^+$/$K^+$ pump activity.

In one aspect of the present invention there is provided an FXYD protein or fragment or variant thereof for use in a method of treating myocardial infarction, stroke, or ischemia reperfusion injury.

In one embodiment the treatment may be commenced within about 24 hours of the infarction, stroke, or reperfusion injury. Preferably the treatment is commenced within about 12 hours of the infarction, stroke, or reperfusion injury, more preferably the treatment is commenced within about 6 hours of the infarction, stroke, or reperfusion injury, even more preferably the treatment is commenced within about 3 hours of the infarction, stroke, or reperfusion injury, most preferably the treatment is commenced at about the time of the infarction, stroke, or reperfusion injury.

In one embodiment the FXYD protein is selected from the group consisting of FXYD1, FXYD3, FXYD4, FXYD6 and FXYD7.

In one embodiment the fragment or variant comprises a reactive cysteine corresponding to Cys62 of FXYD1.

In one aspect of the present invention there is provided use of an FXYD protein or fragment or variant thereof for the manufacture of a medicament for the modulation of $Na^+/K^+$ pump activity in a subject.

In one aspect of the present invention there is provided use of an FXYD protein or fragment or variant thereof for the manufacture of a medicament for the treatment of myocardial infarction, stroke, or ischemia reperfusion injury.

In one embodiment the FXYD protein is selected from the group consisting of FXYD1, FXYD3, FXYD4, FXYD6 and FXYD7.

In one embodiment the fragment or variant comprises a reactive cysteine corresponding to Cys62 of FXYD1.

In one aspect of the present invention there is provided a pharmaceutical composition comprising an FXYD protein or a fragment or variant thereof together with at least one pharmaceutically acceptable adjuvant, excipient or buffer.

In one aspect of the present invention there is provided a method for treating cancer by modulating $Na^+/K^+$ pump activity in a subject, the method comprising administering to said individual a therapeutically effective amount of a loss of function FXYD protein wherein said loss of function FXYD protein increases or maintains glutathionylation of said $Na^+/K^+$ pump thereby modulating $Na^+/K^+$ pump activity.

In one aspect of the present invention there is provided a loss of function FXYD protein or fragment or variant thereof for use in a method of treating cancer.

In one embodiment the loss of function FXYD protein is an FXYD protein or fragment or variant thereof that does not comprise a reactive cysteine corresponding to Cys62 of FXYD1.

In one embodiment the loss of function FXYD protein does not comprise basic amino acids vicinal to cysteine corresponding to Cys62 of FXYD1.

In one embodiment the loss of function FXYD protein is FXYD2 or FXYD5 or a fragment or variant of FXYD2 or FXYD5. In one embodiment the loss of function FXYD protein is a fragment or variant of FXYD3.

In one embodiment the loss of function FXYD protein is administered in a combination treatment with radiotherapy or chemotherapy.

In one embodiment the cancer is selected from the group consisting of breast cancer, prostate cancer, pancreatic cancer and bowel cancer.

In one aspect of the present invention there is provided use of a loss of function FXYD protein for the manufacture of a medicament for the treatment of cancer.

In one aspect of the present invention there is provided an isolated loss of function FXYD protein that does not comprise a reactive cysteine corresponding to Cys62 of FXYD1.

In one embodiment the loss of function FXYD protein does not comprise a cysteine corresponding to Cys62 of FXYD1. In another embodiment the loss of function FXYD protein does not comprise at least one basic amino acid vicinal to a cysteine corresponding to Cys62 of FXYD1.

In one embodiment the isolated loss of function FXYD protein is a variant of FXYD1, FXYD3, FXYD4, FXYD5, FXYD6 or FXYD7.

The summary of the invention described above is not limiting and other features and advantages of the invention will be apparent from the following detailed description of the preferred embodiments, as well as from the claims.

BRIEF DESCRIPTION OF THE DRAWINGS

A preferred embodiment of the present invention will now be described, by way of an example only, with reference to the accompanying drawings wherein:

FIG. 10 is a sequence alignment of partial sequences of Human FXYD proteins 1-7 indicating the position of the cysteines at position 60 and 62 of FXYD1 (light shading) and the basic amino acids at positions 61 and 63 of FXYD1 (dark shading).

DEFINITIONS

Figure 1:
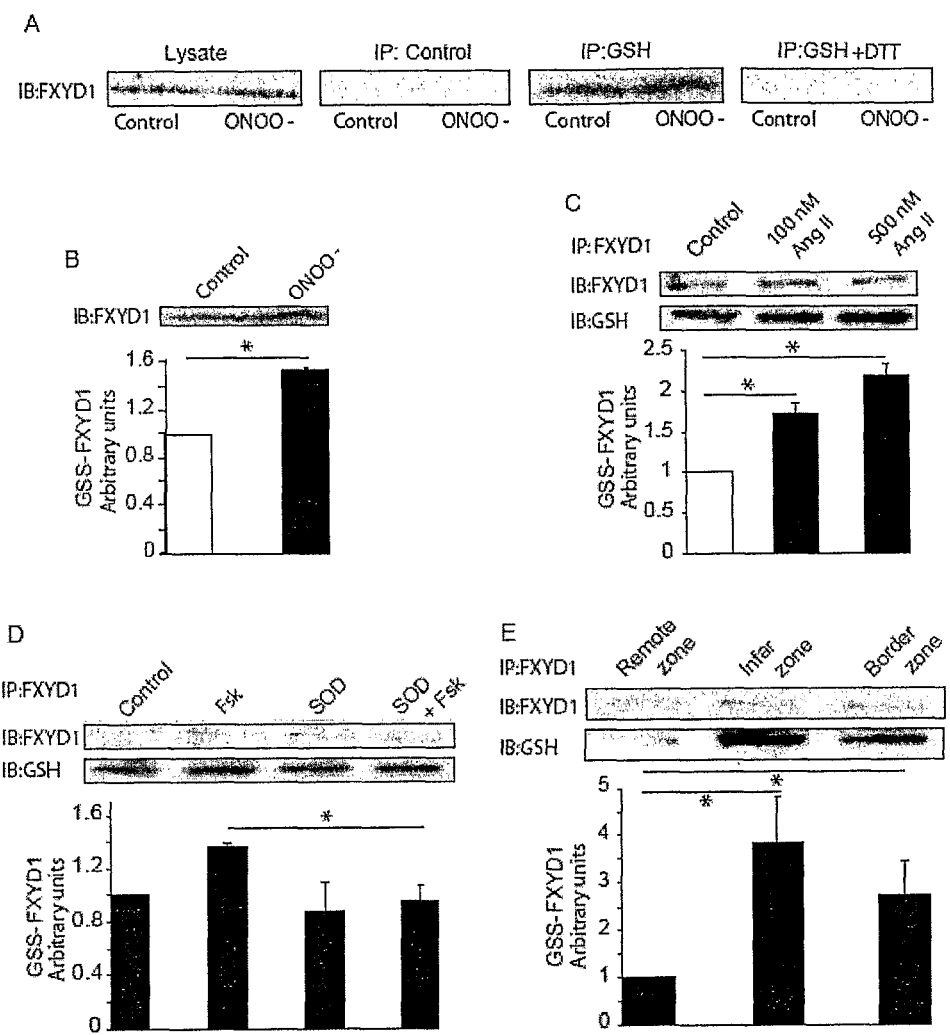
FIG. 1 illustrates glutathionylation of FXYD1 in the myocardium. A. FXYD1 is detected in cell lysate, as well as biotin-tagged glutathionylated subfraction of cell lysate in cardiac myocytes. This occurs at baseline (control: C), and is increased by exposure to the chemical oxidant $ONOO^-$. Negative control was performed using myocytes not loaded with biotin-GSH. No FXYD1 was detected if DTT (1 mmol) was added to the lysate prior to streptavidin precipitation. B. Histogram showing mean densitometry of FXYD1 immunoblots in streptavidin pull-down of myocytes loaded with biotin-GSH exposed to $ONOO^-$ or control (n=3). C. Effect of Ang II (100 and 500 nM) on glutathionylation of FXYD1 as detected by immunoblotting (IB) with GSH antibody against the FXYD1 immunoprecitate (IP). D. Effect of Forskolin (Fsk) (100 nM) on glutathionylation of FXYD1 as detected by the GSH antibody technique in myocytes with and without incubation in pegylated SOD. E. Glutathionylation of FXYD1 in myocardium from a sheep model of infarction. Samples were taken from myocardium remote to the infarct; the peri-infarct zone, and the infarct zone. Histograms summarise densitometry of immunoblots normalized against control (n=3 for each experiment). * $p<0.05$.

The term "therapeutically effective amount" as used herein includes within its meaning a sufficient amount of a compound or composition to provide a desired therapeutic effect. The exact amount required will vary from subject to subject depending on factors such as the species being treated, the age and general condition of the subject, co-morbidities, the severity of the condition being treated, the particular agent being administered and the mode of administration. Thus, for any given case, an appropriate "therapeutically effective amount" may be determined by one of ordinary skill in the art using only routine methods.

The terms "subject" and "patient" are used interchangeably herein and include humans and individuals of any species of social, economic or research importance including but not limited to members of the genus ovine, bovine, equine, porcine, feline, canine, primates, rodents.

The terms "treating" and "treatment" as used herein includes administering is therapy to prevent, cure, alleviate, ameliorate or prevent the symptoms associated with a disorder, disease, injury or condition.

The term "combined with" and similar terms such as "in conjunction with" as used herein in relation to a therapeutic regime means that each of the drugs and other therapeutic agent(s), such as agonists and antagonists or additional substances used in the treatment or prevention of a disease or condition, is used in the treatment of a subject and that each of the drugs and other therapeutic agents in the "combined" therapeutic regime may be administered to the subject simultaneously with one or more of the other agents in the therapeutic regime, or may be administered to the subject at a different time to one or more of the other agents in the therapeutic regime. It will be understood that the term "combined with" and similar terms such as "in conjunction with" as used herein in relation to a therapeutic regime encompasses within their meaning administration of each of the drug(s) and other therapeutic agent(s) via different modes (for example one may be administered orally and another by injection). The term "combined with" and similar terms such as "in conjunction with" when used in relation to a therapeutic regime may mean that any one or more of the drugs or other agents may be physically combined prior to administration to the subject, and it will be understood that the term also includes administration of the one or more drugs and other therapeutic agents as separate agents not in prior physical combination.

The term "comprising" as used herein means including principally, but not necessarily solely. Furthermore, variations of the word "comprising", such as "comprise" and "comprises", have correspondingly varied meanings.

The term, "Ip" as used herein is an abbreviation for the measurable cellular transmembranous current generated by the $Na^+$—$K^+$ pump in experimental situations using a patch clamp technique.

The term "derivative" when used in relation to an FXYD protein of the present invention includes any functionally equivalent FXYD protein including any fusion molecules produced integrally (e.g., by recombinant means) or added post-synthesis (e.g., by chemical means). Such fusions may comprise FXYD proteins of the invention conjugated to a polypeptide (e.g., puromycin or other polypeptide), a small molecule (e.g., psoralen) or an antibody.

The term "modulator" as used herein refers to any entity which can increase or decrease the glutathionylation of the $Na^+/K^+$ pump. Modulators may be is "activators", which decrease the level of glutathionylation and thus facilitate increased $Na^+/K^+$ pump activity. In some embodiments modulators are "inhibitors" which are entities that do not affect the level of $Na^+/K^+$ pump glutathionylation but inhibit endogenous modulators from doing so. In preferred embodiments modulators are FXYD proteins or derivatives thereof.

The terms "FXYD protein" and "FXYD proteins" as used herein refer to any protein, polypeptide or oligopeptide comprising at least a portion of an FXYD protein, variant or homologue thereof and which retain the ability to associate with the $Na^+/K^+$ pump.

In the context of this specification the term "polypeptide" means a polymer made up of amino acids linked together by peptide bonds. The polypeptide may be of any length. Except where the context indicates otherwise it will be understood that the term polypeptide also includes peptides and proteins.

The term "contacting" as used herein refers to exposing tissue, organs or cell to an FXYD protein(s) or prodrugs of the invention so that it can modulate $Na^+/K^+$ pump activity. Contacting may be in vitro, for example by adding the FXYD protein or prodrug to cultured tissue or cells for diagnostic or research purposes or to test for susceptibility of the tissue or cells to the FXYD protein or prodrug. Contacting may be in vivo, for example administering the FXYD protein or prodrug to a subject, such as for treatment or prevention of an undesirable condition.

The term "at least one" when used in the context of a group of selectable elements includes any one, two or more, up to all members of the group, individually selected and includes any combination of the members of the group. Similarly, the term "at least two" when used in the context of a group of selectable elements includes any selection of two or more members of the group in any combination.

To the extent that it is permitted, all references cited herein are incorporated by reference in their entirety.

In the context of this specification the terms "Na$^+$—K$^+$ ATPase", Na/K pump, Na$^+$—K$^+$ pump and Na,K ATPase are used interchangeably.

In the context of this specification the terms "PLM", "phospholemman" and "FXYD1" are used interchangeably.

DETAILED DESCRIPTION

The invention will now be described in more detail, including, by way of is illustration only, with respect to the examples which follow.

In accordance with the present invention compositions and methods are provided for the modulation of Na$^+$/K$^+$ pump glutathionylation, particularly in the treatment of conditions such as myocardial infarction, cancer and stroke. The methods generally comprise either the use of compositions comprising an FXYD protein or an FXYD protein alone for treatment of a condition where the modulation of Na$^+$/K$^+$ pump activity by alteration of Na$^+$/K$^+$ glutathionylation may be beneficial.

Modulation of Na$^+$/K$^+$ Pump Activity

All cells are characterised by a difference in electrical potential between the inside of the cell and the outside, separated by the cell membrane. The electrical and chemical gradient generated across the across the cell membrane by the function of the Na$^+$/K$^+$ pump is critical for a number of processes including excitation-contraction coupling in muscle cells and facilitated transportation of metabolites for example, glucose and amino acids into the cell. Accordingly, modulation of Na$^+$/K$^+$ pump activity plays a critical role in cellular function.

FXYD Proteins

The FXYD proteins are a family of small type I membrane proteins are named after an invariant FXYD signature sequence in the extracellular domain. The mammalian FXYD ("fixit") proteins, expressed in a tissue-specific manner (Sweadner and Rael, 2000), are numbered chronologically according to the dates they were cloned and consist of phospholemman (FXYD1) (Palmer et al., 1991 and for example human FXYD1 UniProtKB/Swiss-Prot Accession No. 000168 (SEQ ID NO. 1)) the Na,K-ATPase γ subunit (FXYD2) (Mercer et al., 1993 and for example human FXYD2 UniProtKB/Swiss-Prot Accession No. P54710 (SEQ ID No. 2)), mammary tumor marker 8, Mat-8 (FXYD3) (Morrison et al., 1995 and for example human FXYD3 Genbank Accession No. CAG46994 (SEQ ID No. 3)), corticosteroid hormone-induced factor CHIF (FXYD4) (Attali et al., 1995 and for example human FXYD4 Genbank Accession No. CAI17065 (SEQ ID No. 4)), protein 'related to ion channel' Ric (FXYD5) (Fu and Kamps, 1997 and for example human FXYD5 Genbank Accession No. AAQ89350 (SEQ ID No. 5)), phosphohippolin (FXYD6) (Yamaguchi et al., 2001 and for example human FXYD6 Genbank Accession No. CAG38488 (SEQ ID No. 6)) and FXYD7 (Béguin et al., 2002 and for example human FXYD7 Genbank Accession No. NP_071289 (SEQ ID No. 7).

Examples of nucleic acid sequences encoding FXYD proteins are, human FXYD1 EMBL-EBI Accession No. U72245 (SEQ ID No. 8), human FXYD2 EMBL-EBI Accession No. U50743 (SEQ ID No. 9), human FXYD3 Genbank Accession No. CR542197 (SEQ ID No. 10), human FXYD4 Genbank Accession No. NM_173160 (SEQ ID No. 11), human FXYD5 Genbank Accession No. NM_001164605 (SEQ ID No. 12), human FXYD6 Genbank Accession No. NM_022003 (SEQ ID No. 13) and human FXYD7 Genbank Accession No. NM_022006 (SEQ ID No. 14).

FIG. 10 illustrates part of a multiple sequence alignment performed using the complete sequences of SEQ ID No's 1-7 (human FXYD1 to FXYD7). FIG. 10 indicates the position of the cysteines at position 60 and 62 of FXYD1 (light shading) and the basic amino acids at positions 61 and 63 of FXYD1 (dark shading). It will be understood that the amino acid numbering as indicated in FIG. 10 and the Sequence Listing is derived from the sequences associated with the accession numbers referenced above. The amino acid numbering in FXYD variants or homologues may vary due to the presence of, for example, a leader peptide however it will be understood that the residues corresponding to the cysteines at positions 60 and 62 of FXYD1 will be located in the cytoplasmic domain near the transmembrane segment.

It will be understood that the invention encompasses variants of FXYD proteins described herein. Typically, a variant is a sequence variant or a naturally occurring variant such a splice variant or a sequence homologue. Typically, the variant retains the ability to interact with the Na—K pump. Variants include those prepared by recombinant or synthetic methods known in the art.

Variants or homologues may have one or more amino acid substitutions, deletions, additions and/or insertions in the amino acid sequence. Variants or homologues of FXYD proteins of the invention preferably exhibit at least about 70%, at least about 80%, at least about 85%, or at least about 90% identity to a native FXYD protein, more preferably at least about 92%, or at least about 97% identity, and most preferably at least about 97% identity across the length of the variant or homologue to a native FXYD protein.

Some native FXYD proteins or fragments thereof may incapable of promoting de-glutathionylation of the Na$^+$—K$^+$ pump. For instance Example 6 shows that FXYD2 does not alter Na$^+$—K$^+$ pump function. From FIG. 10 it can be seen that native FXYD2, FXYD5 and FXYD6 lack at least one of a reactive cysteine corresponding to cys62 of FXYD1 and basic amino acids vicinal to that reactive cysteine. Thus it is contemplated that FXYD5 and FXYD6 would lack an ability to promote deglutathionylation of the Na$^+$—K$^+$ pump.

Accordingly a loss of function FXYD protein variant may therefore be created by mutation of one or more of the basic amino acids vicinal to the reactive cysteine to a non-basic amino acid or by mutation of a reactive cysteine corresponding to cys62 of FXYD1. A gain of function FXYD protein variant may be created from FXYD2, FXYD5 or FXYD6 by mutation of one or more amino acids vicinal to the reactive cysteine to a basic amino acid or in the case of FXYD5, the insertion of a cysteine at a position corresponding to cys62 of FXYD1. In some embodiments a gain of function FXYD5 variant may be created by insertion of a cysteine at a position corresponding to cys62 of FXYD1 and insertion of a basic amino acid at a position corresponding to lys63 of FXYD1.

Variants may be modified by, for example, the deletion or addition of amino acids that influence the ability of the variant to modulate the Na—K pump, secondary structure and hydropathic nature of the polypeptide.

Amino acid substitutions include, but are not necessarily limited to, amino acid substitutions known in the art as "conservative". A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

Typically, a variant FXYD protein differs from a native FXYD protein by substitution, deletion or addition of five amino acids or fewer, such as by four, or is three, or two, or one amino acids.

Typically, an FXYD protein of the invention is an isolated protein. It will be understood that the term "isolated" in this context means that the protein has been removed from or is not associated with some or all other components with which it would be found in the natural system. For example, an "isolated" peptide may be removed from other amino acid sequences within an FXYD polypeptide sequence, or may be removed from natural components such as unrelated proteins. For the sake of clarity, an "isolated" FXYD protein includes an FXYD protein which has been chemically synthesised and includes a polypeptide or oligopeptide which has been prepared by recombinant methods. As described herein the isolated FXYD protein of the invention may be included as a component part of a longer polypeptide or fusion protein.

Accordingly, an FXYD protein of the invention may comprise at least about 6 amino acids to at least about 65 amino acids. Preferably, an FXYD protein of the invention may comprise about 7-10, 11-15, 16-20, 21-25, 26-30, 31-35, 36-40, 41-45, 46-50, 51-55, 56-60 or 61-65 amino acids.

An FXYD protein of the invention may be included as a component part of a longer amino acid sequence. For example, an FXYD protein of the invention may be present within the form of a fusion protein or polypeptide where the FXYD protein is linked with one or more amino acid sequences to which it would not be linked to in nature.

In this context it will be understood that a fusion protein or polypeptide may comprise a plurality of FXYD proteins of the invention, such as a polypeptide where two or more FXYD proteins are present on a single polypeptide.

A fusion protein or polypeptide comprising one or more FXYD proteins of the invention may additionally comprise one or more unrelated sequences. Such a sequence will generally be referred to herein, in the context of a fusion protein or polypeptide, as a "fusion partner". Typically, a fusion partner is an amino acid sequence, and may be a polypeptide. A fusion partner may, for example, be selected to assist with the production of the peptide or peptides. Examples of such fusion partners include those capable of enhancing recombinant expression of the peptide or of a polypeptide comprising the peptide; those capable of facilitating or assisting purification of the peptide or a polypeptide comprising the peptide such as an affinity tag. Alternatively, or in addition, a fusion partner may be selected to increase solubility of the peptide or of a polypeptide comprising the peptide, to increase the immunogenicity of the peptide, to enable the peptide or polypeptide comprising the peptide to be targetted to a specific or desired intracellular compartment.

Methods for the preparation of fusion proteins are known in the art. Typically, a fusion protein may be made by standard techniques such as chemical conjugation, peptide synthesis or recombinant means. A fusion protein may include one or more linker(s), such as peptide linker(s), between component parts of the protein, such as between one or more component peptides, and/or between one or more fusion partners and/or component peptides. Such a peptide linker (s) may be chosen to permit the component parts of the fusion protein to maintain or attain appropriate secondary and tertiary structure.

FXYD proteins of the invention may be prepared by any suitable means, such as by isolation from a naturally occurring form, by chemical synthesis or by recombinant means. The skilled addressee will be aware of standard methods for such preparation, such as by isolation from a naturally occurring longer amino acid sequence by enzymatic cleavage, such as by chemical synthesis, such as by recombinant DNA technology.

A synthesized FXYD protein may be purified by preparative high performance liquid chromatography or other comparable techniques available in the art. If desired, the composition of the synthetic FXYD proteins may be confirmed by amino acid analysis or sequencing. Additionally, the amino acid sequence of a polypeptide, or any part thereof, may be altered during direct synthesis and/or combined using chemical methods with sequences from other proteins, or any part thereof, to produce a variant polypeptide.

The FXYD protein of the invention, or a fusion protein or polypeptide comprising an FXYD protein of the invention as a component part thereof may be a soluble peptide, fusion protein or polypeptide.

The invention provides polynucleotides that encode one or more FXYD protein(s) of the invention and polynucleotides that encode one or more fusion protein(s) or polypeptide(s) comprising FXYD protein(s) of the invention, as described herein. In certain embodiments of the invention, polynucleotide sequences or fragments thereof which encode peptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Polynucleotides may comprise a native sequence (i.e., an endogenous sequence that encodes an FXYD protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native FXYD protein. The effect on the immunogenicity of the encoded polypeptide may generally be assessed as described herein. The term "variants" also encompasses homologous genes of xenogenic origin.

In order to express a desired polypeptide, the nucleotide sequences encoding the peptide, fusion protein or polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

The invention thus provides vectors comprising a polynucleotide sequence of the invention. In one embodiment the vector may be an expression vector. The invention also provides a host cell comprising a polynucleotide or vector of the invention. The invention also provides methods for the preparation of a peptide of the invention, such a method comprising culturing a host cell comprising a polynucleotide or expression vector of the invention under conditions conducive to expression of the encoded peptide. In one embodiment, the method further comprises purifying the expressed peptide.

FXYD proteins are important in disease processes. An FXYD2 mutation has been linked to human, dominant, renal hypomagnesemia (Meij et al., 2000) while overexpression of brain FXYD1 is implicated in Rett syndrome (Deng et al., 2007), and overexpression of FXYD5 plays a role in cancerogenesis. FXYD3 is overexpressed in tumors of organs including breast, pancreas and prostate and underexpressed in tumors of other organs including kidney and colon and in undifferentiated Caco-2 cells suggesting a tissue-specific role of FXYD3 in tumorogenesis and cell differentiation. The level of expression of FXYD3 in tumors of the colon correlate inversely with the response to radiotherapy, i.e., the response is poorer with higher levels of expression.

As described herein further investigation by the inventor demonstrated that FXYD proteins have been implicated in regulation of Na/K pump function. Most interest in the published literature, in terms of a regulatory function, has been focussed on FXYD1 which is unique among the FXYD proteins by having serine amino acid residues in their cytoplasmic terminal that are targets for protein kinases, i.e., they can be phosphorylated. In this scheme it is thought that FXYD proteins inhibit pump activity and that this inhibition is relieved with phosphorylation of FXYD1.

Surprisingly, as described herein, the present inventor has demonstrated that the inclusion of FXYD1 in patch pipette solutions is associated with increased Na/K pump current, which is at odds with the prevailing view that FXYD1 inhibits the pump in cardiac myocytes. The inventor hypothesised that a conserved cysteine in FXYD proteins might be 'reactive' (most cysteines are not) and so included FXYD1 in patch pipette solutions and activated a kinase-dependent oxidative stimulus. As demonstrated herein the exogenous FXYD1 abolished the kinase-dependent decrease in pump activity.

Further investigation by the inventor as described herein demonstrated that the reversal of the oxidation-induced pump inhibition is mediated by exogenous FXYD interaction with glutathionylation and has been shown to be causally related to pump inhibition. Hence exogenous FXYD3 abolished the Na/K pump $\beta_1$ subunit glutathionylation induced by the oxidant stimulus (exposure of myocytes to angiotensin II). The use of an FXYD3 mutant in which the four cysteines of FXYD3 had been mutated to serine failed to elicit the same (abolition) effect. In functional studies on voltage clamped myocytes, an angiotensin II-induced decrease in electrogenic Na/K pump current was abolished by the wild type FXYD3 included in the pipette solutions. Again, this effect was not apparent when the cysteine-free FXYD3 mutant was used.

Accordingly, arising from these studies there is provided herein a method of modulating Na/K pump activity by contacting the pump with an FXYD protein to influence glutathionylation of the pump. Depending on the desired influence on the glutathionylation of the pump, the FXYD protein brought into contact with the pump may be intended to reduce the glutathionylation of the pump, thereby removing or reducing the degree of inhibition of the pump to increase the activity of the pump or it may be to counteract deglutathionylation of the pump thereby maintaining or exacerbating inhibition of pump activity. Briefly stated, therefore, where pump activity is desired to be increased (such as by diminishing glutathionylation-induced inhibition of the pump) this may be achieved, for example, by contacting the pump with an FXYD protein capable of promoting deglutathionylation of the pump. Examples of such situations in a therapeutic context include myocardial infarction, stroke or other conditions of tissue injury arising form from ischaemia or reperfusion. Alternatively, where pump activity is desired to be inhibited (such as by maintaining the pump in a glutathione-induced inhibited state) this may be achieved by contacting the pump with an FXYD protein incapable of promoting deglutathionylation of the pump and displacing the functional wild type, native FXYD protein. As explained herein, an FXYD protein incapable of (or with reduced capability to) deglutathionylation of the Na/K pump is referred to as a loss of function FXYD protein. Examples of such situations in a therapeutic context include treatment of cancer, and in particular treatment of breast, prostate or pancreatic cancer where FXYD proteins are overexpressed and, as described herein, may assist the cancer cells to overcome the otherwise inhibitory effects of oxidative stress-induced glutathionylation.

In one embodiment an FXYD protein derivative with no reactive cysteine or critical vicinal basic amino acid residues may be administered to displace a wild-type FXYD protein and eliminate its protection of $Na^+$—$K^+$ pump function from an increased oxidative load in cancer cells. This may be facilitated by coupling of the FXYD protein to a peptide to selectively target membrane-soluble compounds to cancer cells. This may enhance the efficacy and reduce unwanted effects in non-target tissues. In a further embodiment targeting of the FXYD protein cancer cells may improve the efficacy of conventional treatments administered in combination or conjunction with the FXYD protein such as radiotherapy or chemotherapeutic approaches that also increase oxidative loads in cells.

Each of these general applications provided by the present invention, namely promotion of deglutathionylation by FXYD proteins and inhibition of deglutathionylation by loss of function FXYD proteins, will now be described in more detail.

Figure 6:
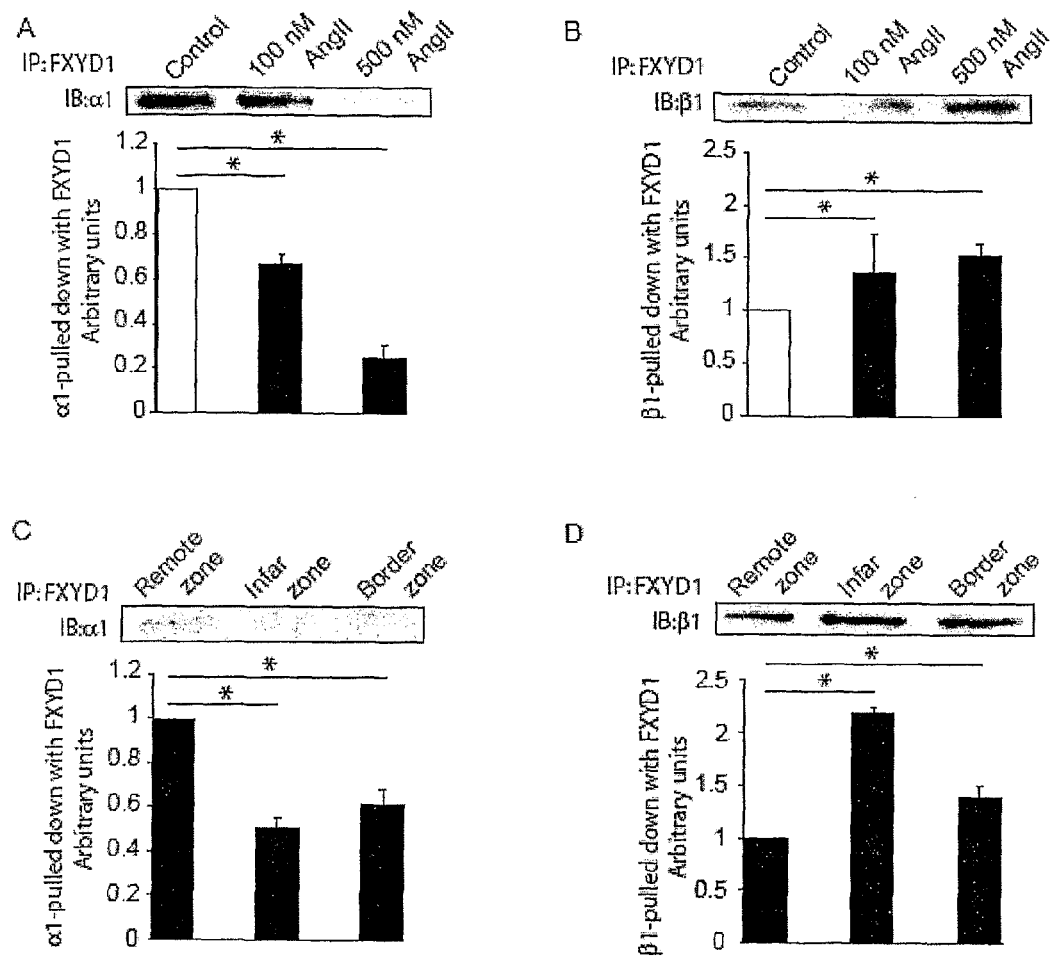
FIG. 6 illustrates that oxidative stimuli decrease interaction of FXYD1 with $\alpha_1$ and increase interaction with $\beta_1$ Na⁺—K⁺ pump subunits in myocardium. A. Effect of Ang II (100 nM and 500 nM) on densitometry of $\alpha_1$ subunit immunoblot (IB) against FXYD1 immunoprecipitate (IP) in rabbit cardiac myocytes. B. Effect of Ang II (100 nM and 500 nM) on densitometry of $\beta_1$ subunit immunoblot (IB) in FXYD1 immunoprecipitate (IP) in rabbit cardiac myocytes. C. $\alpha_1$ subunit (C) and $\beta_1$ subunit (D) immunoblot of FXYD1 immunoprecipitate of lysate from myocardium of a sheep model of infarction. Myocardium from region remote from the infarct; as well as the peri-infarct and infarct zone was used. In all experiments, FXYD1 immunoblot against the FXYD1 immunoprecipitate is shown. Histograms summarise densitometry of immunoblots normalized against control (n=3 for each experiment). * p<0.05.

FXYD Proteins in Treatment of Infarction—Reversal of Oxidative $Na^+$—$K^+$ Pump Inhibition As described herein myocardial infarction is associated with a marked increase in glutathionylation of FXYD1 (See FIG. 1), a decrease of its "normal" association with the Na—K pump's α subunit and an increase in association the $\beta_1$ subunit (See FIG. 6), consistent with a role of FXYD1 in de-glutathionylation of the $\beta_1$ subunit. The inventor has previously also described that myocardial infarction is associated with glutathionylation of the Na—K pump's β1 subunit and that this glutathionylation is causally related to pump inhibition.

Accordingly, exogenously administered FXYD protein facilitates deglutathionylation of the $Na^+$—$K^+$ pump's $\beta_1$ subunit, activation of function and reversal of the adverse effects of cellular $Na^+$ and $Ca^{2+}$ overload. Supply of exogenous antioxidants or attempts to increase intracellular GSH (as has been studied extensively) may not have been useful since spontaneous rates of deglutathionylation, driven by a favourable redox potential alone, is very slow. An oxidoreductase-like effect, based on the reactive cysteine residue that catalyses de-glutathionylation identified in the present invention is more effective.

In one aspect the invention thus provides a method for the treatment or prevention of a condition associated with glutathionylation-induced inhibition of a Na/K pump, the method comprising contacting a Na/K pump with a therapeutically effective amount of an FXYD protein. In this manner, the FXYD protein facilitates de-glutathionylation of the $Na^+$—$K^+$ pump.

Any suitable FXYD protein may be used. In the context of restoration of pump activity or diminishing glutathione-induced pump inhibition, a suitable FXYD protein is any FXYD protein or derivative thereof that has an ability to promote deglutathionylation of the Na/K pump. As described herein there are currently known seven human FXYD proteins examples of which are represented by the amino acid and nucleic acid sequences in SEQ ID Nos:1-14. Any human FXYD proteins or homologous proteins from non-human species, such as other mammalian species, as well as any functional isoforms thereof, capable of deglutathionylation of the Na/K pump are contemplated for use in this aspect of the invention. Preferably, the FXYD protein is FXYD1, FXYD3, FXYD4, or FXYD7.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 3rd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4.sup.th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds.); and "PCR: The Polymerase Chain Reaction", (Mullis et al., eds., 1994), the contents of each of which are incorporated herein by reference in their entirety.

The FXYD protein may be isolated from a naturally occurring source or may be produced by synthetic means. Methods for the isolation of proteins and their precursors from naturally occurring sources are known in the art and include methods and references cited above. Methods for the production of proteins and their precursors by synthetic means are also known in the art and include peptide synthesis, such as by chemical synthesis, and recombinant expression of proteins and polypeptides, such as described in references cited above.

As described herein (see Example 5) mutational studies on FXYD proteins expressed in *Xenopus* oocytes identified a specific "reactive" (i.e. susceptible to glutathionylation) cysteine, involved in de-glutathionylation of the $Na^+/K^+$ pump and reversal of pump-inhibition as the cysteine corresponding to Cys62 of FXYD1. An FXYD protein useful in the methods of the invention for promoting deglutathionylation of the Na/K pump typically comprises a reactive cysteine at a position corresponding to Cys62 of FXYD1. Included in the invention are derivatives and variants of FXYD proteins which maintain or have imparted on them the ability to promote deglutathionylation of a Na/K pump. Examples of derivatives and variants include fragments of FXYD proteins. For example, human FXYD1 is 92 amino acids in length, comprising an extracellular region, a transmembrane region and a cytoplasmic region. As will be appreciated by the skilled addressee, fragments of many proteins retain functional properties of the full length or naturally occurring protein. In the present circumstances, it is envisaged that a fragment of an FXYD protein that is capable of promoting deglutathionylation of a Na/K pump, where the fragment retains a reactive cysteine, such as Cys62 of FXYD1 or a cysteine corresponding thereto, will also be functional in the methods of the invention. Similarly, fragments of other FXYD proteins in which a reactive cysteine is retained are also within the scope of the invention. Reduction of the size of the FXYD protein in such a manner may be beneficial, for example due to greater ease of manufacture compared to a longer therapeutic entity. In an example, the FXYD protein may be an FXYD fragment resulting from deletion of some, most or all of the extracellular domain of the wild type protein. In another example the FXYD protein may be an FXYD fragment resulting from deletion of some of the cytoplasmic domain between the reactive cysteine near the transmembrane segment identified herein and the carboxyl terminal.

FXYD proteins useful in the invention also include those which are derivatives of wild type proteins and include derivatives which have imparted upon them an ability or an increased ability to promote deglutathionylation of a Na/K pump. An example of such a derivative is illustrated by the following.

Mutational studies on FXYD proteins indicate that basic amino acids vicinal to the reactive cysteine, in particular basic amino acids at positions corresponding to Arg61 and Lys63 of FXYD1, are influential in glutathionylation of FXYD proteins and hence in the ability of an FXYD protein to promote deglutathionylation of a Na/K pump. Wild type FXYD2 protein, for example, is demonstrated herein to be unable to promote deglutathionylation of a Na/K pump. It is believed that this inability is at least in part due to the absence of basic amino acids vicinal to the cysteine which, in the presence of basic amino acids would be a reactive cysteine. FXYD2 includes the is non-basic amino acid glycine at a position corresponding to Lys63 of FXYD1. It is envisaged that mutation of that glycine to a basic amino acid, such as to lysine or arginine, would impart upon the resultant variant FXYD2 protein an ability to promote deglutathionylation of Na/K pump.

FXYD proteins are lipid- and hence membrane-soluble. Thus administration of FXYD proteins in the setting of acute ischaemic injury may be used, e.g. FXYD1 in the treatment of for example infarction and ischaemia reperfusion injury. The proteins may be administered intravenously, or directly infused into an infarct-related artery for example in the setting of acute intervention with angioplasty procedures. In other embodiments an infusion of an FXYD protein may be administered on a time scale of minutes to hours.

In some embodiments fragments of FXYD proteins which retain the ability to associate with the $Na^+$—$K^+$ pump may be useful. Such FXYD proteins would preferably have optimal properties in terms of modulating the glutathionylation state of the $Na^+$—$K^+$ pump as well as ability to insert in membranes and associate with target proteins are anticipated to be useful in the methods of the present invention. In addition, the size of FXYD protein may be reduced by eliminating a substantial portion of the extracellular domain as well as a substantial portion of the cytoplasmic domain.

In some embodiments FXYD proteins of the present invention may be produced with or conjugated to proteins, polypeptides, oligopeptides, antibodies or fragments thereof, radioactive particles, nanoparticles or microparticles.

FXYD Proteins in Treatment of Cancer—Oxidative $Na^+$—$K^+$ Pump Inhibition

Many cancer tissues such as breast cancer and prostate cancer tissues are known to have high levels of oxidative stress and have developed increased antioxidant defences, specifically of the cytosolic oxidoreductase system. These are established targets in cancer treatment. Through the identification herein of the ability of the FXYD proteins to promote deglutathionylation of the Na/K pump, thereby reducing inhibition of pump activity in conditions of oxidative stress, the present inventor has identified a link between the antioxidant defences of the cancer cells and the apparent overexpression of FXYD proteins. Interruption of that antioxidant defence system in the cancer cell, by interrupting the ability of the FXYD protein to promote deglutathionylation of the pump, is proposed herein as a method to inhibit the growth, spread or metastasis of cancer cells.

As disclosed herein the demonstration that a particular cysteine residue is "reactive" and plays a role in reversal of oxidative Na—K pump inhibition indicates a survival advantage for cancer cells to overexpress FXYD proteins and allows specific targeting of that role in the cells antioxidant defences.

Accordingly, in an aspect of the invention there is provided a method of treating cancer, the method comprising contacting a Na/K pump of a cancer cell with a therapeutically effective amount of a loss of function FXYD protein. In this manner, the loss of function FXYD protein facilitates replacement of an endogenous FXYD protein which is considered to permit de-glutathionylation of the $Na^+$—$K^+$ pump, thereby permitting the Na/K pump to retain activity despite the oxidative stress typical of cancer cells.

As used herein the term "loss of function FXYD protein" refers to any FXYD protein which does not have the ability to promote deglutathionylation of Na/K pump or in which that ability is reduced by comparison to a wild-type FXYD protein. That inability or relative inability may be to a natural inability of the FXYD protein to promote deglutathionylation, such as is illustrated herein by FXYD2, or may be due to one or more mutations made in the FXYD protein.

As an example, it is demonstrated herein a reactive cysteine, corresponding to cys62 of FXYD1 is involved in the ability of an FXYD protein to be glutathionylated and hence in the ability of the FXYD protein to promote the deglutathionylation of the Na/K pump.

As another example, it is demonstrated herein that the basic amino acids vicinal to a reactive cysteine, corresponding to cys62 of FXYD1, such as Arg61 and Lys63 in FXYD1 are influential in the reactivity of the cysteine and so in the ability of an FXYD protein to be glutathionylated and hence in the ability of the FXYD protein to promote the deglutathionylation of the Na/K pump.

With reference to FIG. 10 it can be seen that native FXYD2, FXYD5 and FXYD6 lack at least one of a reactive cysteine corresponding to cys62 of FXYD1 and basic amino acids vicinal to that reactive cysteine. As shown in Example 6, FXYD2 has no effect on $Na^+$—$K^+$ pump function. Thus it is contemplated that FXYD5 and FXYD6 would lack an ability to promote deglutathionylation of the Na/K pump.

A loss of function FXYD protein may therefore be created by mutation of one or more of the basic amino acids vicinal to the reactive cysteine to a non-basic amino acid.

The loss of function FXYD protein may or may not retain other biological functions or characteristics of an FXYD protein.

FXYD proteins generally are described herein, such as in the section describing the proteins useful in the method of the invention for the prevention or treatment of myocardial infarction, stroke and reperfusion. It will be understood that the loss of function FXYD proteins envisaged as useful for inhibiting deglutathionylation of Na/K pump, such as in the treatment of cancer, includes FXYD proteins, derivatives and variants thereof described in the section detailing functional FXYD proteins (ie., those capable of promoting deglutathionylation of an Na/K pump) with the proviso that the loss of function FXYD proteins does not have the ability to promote deglutathionylation of Na/K pump or in which that ability is reduced by comparison to a wild-type FXYD protein.

In the case of a mutant loss of function FXYD protein any reduction of ability to promote de-glutathionylation of the Na/K pump compared to wild-type FXYD protein is encompassed by the term although preferably there will be a greater than about 50% reduction of that ability. More preferably the reduction will be greater than about 60%, or greater than about 70% or greater than about 80%. In the more preferred embodiments the reduction of ability is substantially complete, such as greater than about 90%. More preferably still the loss of function FXYD protein would exhibit complete absence of the ability to promote deglutathionylation of the Na/K pump which for practical purposes is considered to be a reduction of greater than about 95% compared to a wild type FXYD protein.

The identification of the reactive FXYD site allows an approach using a "loss of function" FXYD protein such as the FXYD proteins lacking a reactive cysteine or one or more basic amino acids vicinal to the that cysteine that, when administered, replaces native FXYD proteins. A "loss of function" protein is anticipated to be more effective than an effect that develops over days with conventional techniques such as gene-silencing which may allow time for compensatory mechanisms to develop.

Figure 4:
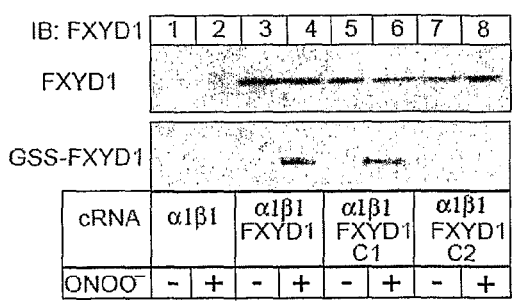
FIG. 4 illustrates the identification of cysteine residue implicated in FXYD1 glutathionylation and Na⁺—K⁺ pump regulation via mutational studies. *Xenopus* oocytes expressing *Xenopus* Na,K-ATPase $\alpha_1$ and $\beta_1$ subunits alone or together with wild type or mutated FXYD1 (FXYDC1, FXYDC2, or FXYDC1C2) were injected with biotin-GSH for detection of glutathionylation, and ONOO— as indicated. A. FXYD1 immunoblot of oocyte microsomes which had been either directly loaded on gels (upper panel) or immunoprecipitated with streptavidin beads (lower panel). B. Histogram showing mean densitometry of GSS-FXYD1 immunoblot normalized against control (GSS-FXYD1 in oocytes expressing native FXYD1/$\alpha_1$/$\beta_1$ subunits and exposed to ONOO⁻). C. $\beta_1$ subunit immunoblot of oocyte microsomes which had been either directly loaded on gels (upper panel) or immunoprecipitated with streptavidin beads (lower panel). D. Histogram showing mean densitometry of GSS-$\beta_1$ immunoblot normalized by the total amount of proteins expressed. For technical reasons, it was not possible to compare glutathionylation of FXYD1 and β subunits for all conditions in the same experiment. Therefore, quantifications do not include glutathionylation of β subunits in oocytes expressing $\alpha_1\beta_1$ subunits without FXYD1. Data from oocytes expressing α, β and FXYD1 or α, β and FXYD1C1C2 subunits were arbitrarily set to 1. Shown are means±SE of 4 independent experiments. * p<0.05. E. Identification of FXYD cysteine implicated in the reversion of maximal pump current inhibition. Currents measured in non-injected oocytes represented 69.5 nA±2.5 and 62.5 nA±1.9 in absence and presence of ONOO⁻, respectively, and were not subtracted. Shown are means±SE from 20 oocytes from 4 different batches. *p<0.05 versus control. C1 =C60/A; C2= C62/A; C1C2= C60/A, C62/A.
Figure 4:
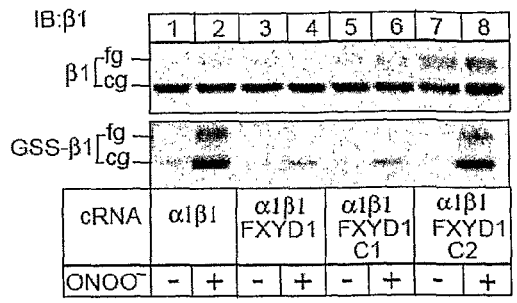
Figure 4:
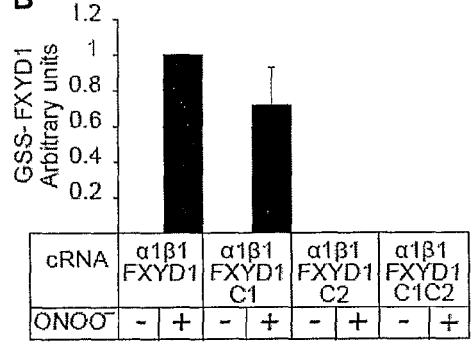
Figure 4:
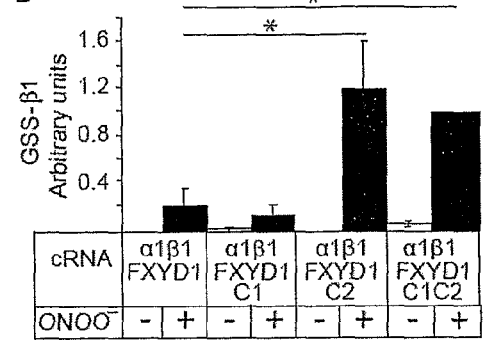
Figure 4:
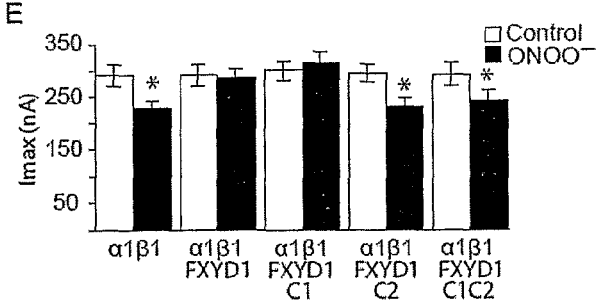

A "loss of function" application is proposed to be useful in cancer treatment by developing a therapeutic "loss-of-function" molecule, such as a molecule with the active site eliminated by mutation of the reactive cysteine or critical vicinal basic amino acid residues (See Examples 5 and 6). Such a molecule may displace wild-type FXYD3 and reduce or eliminate its "oxidoreductase-like" effect. As a consequence it would be expected that the intrinsic oxidative stress in a cancerous cell may cause $Na^+$—$K^+$ pump inhibition and decrease cell viability. The data presented herein (See Example 5 and FIG. 4) indicate that such displacement and loss of function is possible.

In general, studies on animals indicate that knock-out of FXYD genes is not fatal with only minor phenotypic abnormalities apparent. This suggests that FXYD proteins are of particular importance in conditions of oxidative stress and it may not be harmful to administer a "loss-of-function" FXYD mutant even if in doing so FXYD function in non-target tissues is transiently eliminated. On the other hand, acute effects of administering a "loss-of-function" FXYD mutant may be less readily compensated for than long-term effects with adaptations having developed pre-birth, and selective targeting of tissues and/or protection of non-target tissue should be considered.

As described herein (see Example 5) mutational studies on FXYD proteins expressed in *Xenopus* oocytes identified a specific "reactive" (i.e. susceptible to glutathionylation) cysteine, involved in de-glutathionylation of the $Na^+/K^+$ pump and reversal of pump-inhibition as the cysteine corresponding to Cys62 of FXYD1.

Accordingly in some embodiments the cysteine corresponding to Cys62 of FXYD1 in FXYD proteins of the present invention may be mutated to any other residue such that the FXYD protein does not affect glutathionylation of the $Na^+/K^+$ pump. In preferred embodiments the reactive cysteine may be mutated to any one of Alanine, Arginine, Asparagine, Aspartate, Glutamine, Glutamate, Glycine, Histidine, Isoleucine, Leucine, Lysine, Methionine, Phenylalanine, Proline, Serine, Threonine, Tryptophan or Valine.

As described herein (see Example 6) mutational studies on FXYD proteins indicate that basic amino acids vicinal to the reactive cysteine, in particular basic amino acids at positions corresponding to Arg61 and Lys63 of FXYD1 are also influential in glutathionylation of FXYD proteins.

Accordingly in some embodiments at least one of the basic amino acids corresponding to Arg61 and Lys63 of FXYD1 in the FXYD proteins of the present invention may mutated to any non-basic amino acid. The non-basic amino acid may be any one of Alanine, Asparagine, Aspartate, Glutamine, Glutamate, Glycine, Isoleucine, Leucine, Methionine, Phenylalanine, Proline, Serine, Threonine, Tryptophan or Valine.

In some embodiments FXYD proteins of the present invention may be produced with or conjugated to proteins, polypeptides, oligopeptides, antibodies or fragments thereof, radioactive particles, nanoparticles or microparticles.

It is also envisaged that an FXYD protein may be associated with a compound which specifically targets cancer tissues, based on specific properties the tumour but not non-target tissues. For example, an approach developed for targeting prostate cancer with a compound expected to be toxic to all cells in the body (Thapsigargin) may be adapted for use with "loss-of-function" FXYD mutants. With this approach, the FXYD protein is coupled to a water-soluble (and hence membrane-impermeable peptide (e.g. HSSKLQ) to create an FXYD prodrug that is inactive because it cannot cross cell membranes. The peptide is designed to be a selective substrate for prostate cancer-specific proteases (e.g. the chymotrypsin-like serine protease Prostate-Specific Antigen (widely known from the "PSA-test") secreted by the cancer cells and only enzymatically active is the tissue fluid immediately surrounding the cells. When the HSSKLQ peptide is cleaved off the FXYD prodrug, the active lipophilic molecule can enter the cell membrane and then modulate $Na^+$—$K^+$ pump activity. If the active FXYD mutant is a significant substrate for the relevant proteases itself, it may be possible to modify the FXYD mutant with amino acid substitutions (e.g. of serines) to make it protease-resistant.

In another embodiment, inhibition of endogenous FXYD effects may be achieved by targeting the reactive cysteine in the cytosolic domain of an FXYD protein. The loss of function mutations referred to above may be introduced into or synthesised in a peptide fragment of the cytosolic domain of an FXYD protein to generate a peptide blocker. These peptide blockers may be able to cross the membrane when attached to the tat-peptide, known in the art to deliver other blocking compounds into cells.

As described herein oxidative stress and a role of FXYD3 as a "membrane-oxidoreductase" appears to be the common link between FXYD3 and the $Na^+$—$K^+$ pump as therapeutic targets in cancer treatment. On that basis it is expected that a therapeutic intervention that enhances oxidative stress might be augmented with $Na^+$—$K^+$ pump inhibition. Consistent with this, ouabain enhances irradiation damage to human tumour cell lines but not normal cell lines, and it has been suggested that cardiac glycosides might enhance the therapeutic index of radiotherapy (Mijatovic et al., 2007). Since much of the effect of radiotherapy is mediated by the increase in oxidative stress it induces, a "loss-of-function" molecule designed to eliminate FXYD3 might be particularly efficacious in enhancing the benefit of radiotherapy. However, a "loss-of-function" molecule might also be a useful adjuvant to chemotherapeutic agents since many of these also increase oxidative stress.

Treatment Regimen

The most appropriate treatment regime for any particular patient may be determined by the treating physician and will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

The present inventors envisage that a clinically significant alteration of glutathionylation of the $Na^+$—$K^+$ pump may be experienced if FXYD proteins were to be given to patients with a condition associated with oxidative inhibition of the $Na^+/K^+$ pump.

In one aspect of the present invention, the administration of one or more FXYD proteins may be as an "add-on", in which a patient may be treated with a conventional drug. For example a FXYD protein may be administered before, during or after a treatment with, for example with a chemotherapeutic agent or radiotherapy. Consequently, it will be appreciated that in this context the term "add-on" refers to an additional therapeutic integer (the FXYD protein); it does not mean that the FXYD protein must be added as the last drug. The order and composition of the specific drugs and drug classes in the combination therapy may be determined by the skilled addressee, and may include, for example where the therapeutic regime involves the administration of multiple drug classes, the FXYD proteins may be administered at any stage during the regimen.

As a further example of a treatment regime of the method of the invention, the condition of a patient suffering a myocardial infarction may be at least partially stabilized prior to administration of the one or more FXYD proteins. Furthermore, the condition of a patient may be at least partially stabilized prior to commencement of a method of the invention. Either of such treatment regimes may be referred to as first stabilizing a patient.

As a further example of a treatment regime, a FXYD protein may be the first drug to be administered in the treatment of myocardial infarction without any prior medication or stabilisation. The FXYD proteins proposed for the present invention may be administered as compositions either therapeutically or preventively. In a therapeutic application, compositions are administered to a patient already having a condition associated with oxidative inhibition of the $Na^+/K^+$ pump, in an amount sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine. One skilled in the art would be able, by routine experimentation, to determine an effective, amount of the FYXD protein, and other agents where appropriate, which would be required to treat the condition. Generally, an effective dosage is expected to be in the range of about 0.00001 mg to about 1000 mg per kg body weight per 24 hours; typically in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours. Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In some embodiments treatment would be commenced as soon as possible after an infarction or a stroke or at about the same time as reperfusion. For example the treatment may be commenced in conjunction with a conventional therapy for facilitation of reperfusion such as angioplasty. In other embodiments the treatment would be commenced within about 15 minutes to one hour, or about one hour to about three hours, or about three hours to about six hours, or about six hours to about nine hours, or about nine hours to about 12 hours, or about 12 hours to about 15 hours, or about 15 hours to about 18 hours, or about 18 hours to about 21 hours or about 21 hours to about 24 hours after an infarction, stroke, or reperfusion injury.

Further, it will be apparent to one of ordinary skill in the art that the optimal quantity and spacing of individual dosages and, where combination therapy is used, optimal quantity and spacing of administration of the various agents of the combination therapy, will be determined by the nature and extent of the disease condition or state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition or compositions given per day for a defined number of days, can be ascertained by those skilled in the art using o conventional course of treatment determination tests.

Pharmaceutical Compositions

In general, suitable compositions may be prepared according to methods which are known to those of ordinary skill in the art and accordingly may include a pharmaceutically acceptable carrier, diluent, excipient and/or adjuvant.

These compositions can be administered by standard routes. In general, the compositions may be administered by the parenteral (e.g., intravenous, intraspinal, subcutaneous or intramuscular). Preferably administration is by the parenteral route.

The carriers, diluents, excipients and adjuvants must be "acceptable" in terms of being compatible with the other ingredients of the composition, and not deleterious to the recipient thereof. Examples of pharmaceutically acceptable carriers or diluents are demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; DMSO, N,N-dimethylacetamide (DMA), lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The composition may include agents which increase the bioavailability or therapeutic duration of the active compound or compounds.

The compositions of the invention may be in a form suitable for parenteral administration, such as, subcutaneous, intramuscular or intravenous injection or infusion.

For administration as an injectable solution or suspension, non-toxic parenterally acceptable diluents or carriers can include, Ringer's solution, isotonic saline, phosphate buffered saline, ethanol and 1,2 propylene glycol.

Adjuvants typically include emollients, emulsifiers, thickening agents, preservatives, bactericides and buffering agents.

As FXYD proteins are lipid soluble the compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell is Biology, Volume XIV, Academic Press, New York, N.Y. (1976), p. 33 et seq., the contents of which is incorporated herein by reference.

The present invention will now be further described in greater detail by reference to the following specific examples, which should not be construed as in any way limiting the scope of the invention.

EXAMPLES

Example 1

FXYD1 is Glutathionylated by Receptor-Coupled Oxidative Stimuli and Under Pathophysiological Conditions To determine if FXYD1 has reactive cysteine residues susceptible to glutathionylation, myocytes were loaded with biotin-tagged GSH (biotin-GSH). They were lysed and biotin-tagged glutathionylated proteins were precipitated using streptavidin beads. The immunoprecipitate was immunoblotted with a FXYD1 antibody. FIG. 1A shows that FXYD1 was easily detectable in total cell lysate, consistent with its abundant expression in cardiac myocytes. It was also detected in the biotin-tagged, glutathionylated subfraction, but not the non-immune IgG immunoprecipate (negative) control. Exposure of the myocytes to 100 µM peroxynitrite (ONOO$^-$) for 10 min prior to lysis substantially increased the amount of FXYD1 in the glutathionylated protein subfraction (FIG. 1B) but had no effect on the detection of FXYD1 in total cell lysate. FIG. 1A shows that the biotin-tagged glutathionylated FXYD1 was not detected when the lysate was incubated with 1 mmol/L DTT prior to precipitation by streptavidin. This sensitivity to 1 mmol/L DTT is supportive of a mixed disulfide bond between FXYD1 and GSH (Chow et al., 1992).

To examine whether a receptor-coupled oxidative signal could increase glutathionylation of FXYD1 from baseline glutathionylation was detected by immunoprecipitation FXYD1 and immunoblotting with an antibody against a glutathionylated cysteine epitope (GSH antibody). Exposure of myocytes to Ang II, known to activate cardiac NADPH oxidase (White et al., 2009), increased glutathionylation of FXYD1 (FIG. 1C). Similarly, the direct activator of adenyl cyclase forskolin, which has recently been shown to activate cardiac NADPH oxidase and increase glutathionylation of the Na$^+$—K$^+$ pump's $\beta_1$ subunit (Figtree et al. 2009; White et al, 2010), increased FXYD1 glutathionylation. This was abolished when myocytes were incubated with membrane permeable pegylated superoxide dismutase (SOD; FIG. 1D) to dismutate superoxide.

To determine if pathophysiological conditions known to be associated with increased oxidative stress may induce glutathionylation of FXYD1 myocardium from a sheep model of infarction (Figtree et al., 2009) was examined. As shown in FIG. 1E, FXYD1 from myocardium in the infarct and peri-infarct zone showed increased glutathionylation compared with that in normal myocardium.

Example 2

Figure 2:
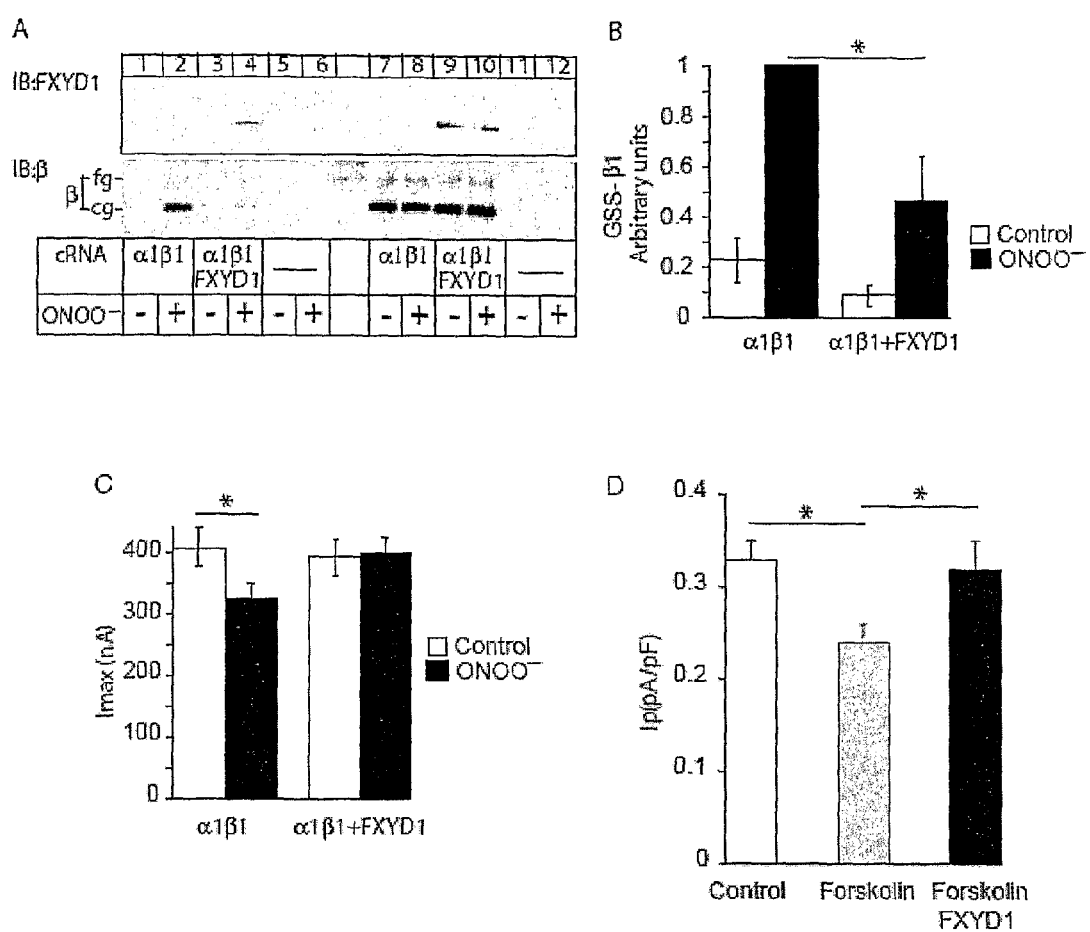
FIG. 2 illustrates glutathionylation of FXYD1 and functional effects. A. FXYD1 (upper panel) and $\beta 1$ subunit (lower panel) immunoblots of oocyte microsomes that were either directly loaded on gels (lanes 7-12) or immunoprecipitated with streptavidin beads (lanes 1-6). Experiments were performed 2 days after injection of *Xenopus* Na,K-ATPase $\alpha_1$ and $\beta_1$ subunit cRNAs alone or together with FXYD1 cRNA. All oocytes were injected with biotin-GSH as described in methods, and with ONOO— as indicated. cg, core glycosylated; fg, fully glycosylated $\beta$ subunit. B. Quantification of glutathionylation of Na,K-ATPase $\beta$ subunit. Shown are arbitrary units obtained by densitometric scanning of data shown in A, normalized by the total amount of proteins expressed. Data from oocytes expressing $\alpha_1\beta_1$ were arbitrarily set to 1. Shown are means±SE of 5 independent experiments. *$p<0.005$. C. FXYD1 reverses Na,K-pump inhibition in the presence of $ONOO^-$. Maximal Na,K-ATPase current (Imax) was measured by the two electrode voltage clamp technique. Shown are means±SE from 20 oocytes from 2 different batches. * $p<0.05$ versus control. Currents measured in non-injected oocytes represented 51 nA±3.5 and 40 nA±2.7 in absence and presence of ($ONOO^-$, respectively, and were not subtracted. D. Effect of FXYD1 on forskolin-induced $Na^+K^+$ pump inhibition in cardiac myocytes. The histogram shows $Na^+$—$K^+$ pump current ($I_p$) of myocytes exposed to forskolin with or without recombinant FXYD1 (500 nM) included in the patch-pipette solution. The number of myocytes in each experimental group ranged from 6 to 10. * indicates $p<0.05$ in all panels.

FXYD1 Reduces Oxidative Modification of the Na$^+$—K$^+$ Pump's $\beta_1$ Subunit, and Abolishes Oxidant-Induced Pump Inhibition Xenopus $\alpha_1$ and $\beta_1$ Na$^+$—K$^+$ pump subunits were overexpressed with dog FXYD1 in Xenopus oocytes. The oocytes had been injected with biotin-GSH to allow detection of glutathionylation. FIG. 2A shows Western blots of microsomes directly loaded onto gels in lanes 7-12 and or immunoprecipitated with streptavidin beads in lanes 1-6. Oxidation had been induced by injection of oocytes with ONOO$^-$ as indicated. Lanes 7-12 show that FXYD1 was detected in microsomes from cRNA-injected oocytes but not detected in microsomes from non-injected oocytes. As shown in the immunoblots in lanes 7-12 in the lower panels, most $\beta_1$ subunits were core-glycosylated after 2 days of expression reflecting the continuous synthesis from injected cRNA. However, a population of fully glycosylated subunits also appeared. Consistent with a low endogenous expression of oocyte subunits (Geering, 1991), a signal for $\beta_1$ subunits in microsomes from non-injected oocytes was barely detectable.

In agreement with results obtained in cardiac myocytes, the immunoblot of the glutathionylated subfraction in lanes 1-6 show that ONOO$^-$ induced glutathionylation of expressed FXYD1 (FIG. 2A, 2B). Since glutathionylation of the $\beta_1$ subunit causes Na$^+$—K$^+$ pump inhibition (Figtree et al., 2009), the effect of FXYD1 on $\beta_1$ subunit glutathionylation on function was examined. Maximal electrogenic Na$^+$—K$^+$ pump current ($I_{max}$) in Xenopus oocytes overexpressing the Na$^+$—K$^+$ pump's $\alpha_1$ and $\beta_1$ subunits with or without expression of FXYD1 was measured. ONOO$^-$ induced a decrease in $I_{max}$ as shown in FIG. 2C. Co-expression of FXYD1 had no effect on $I_{max}$. However, as shown in FIG. 2C, it abolished the decrease induced by ONOO$^-$, in parallel with the effect of co-expression of FXYD1 on $\beta_1$ subunit glutathionylation shown in panels A and B.

FXYD1 is readily inserted into lipid bi-layers of a composition mimicking sarcolemmal membranes and aligns in the correct orientation (Crowell et al., 2003). To examine if exogenous FXYD1 has a functional effect on Na$^+$—K$^+$ pump inhibition induced by an oxidant signal in cardiac myocytes electrogenic Na$^+$—K$^+$ pump current ($I_p$, identified as the ouabain-sensitive membrane current) was measured in ventricular myocytes voltage-clamped with wide-tipped patch pipettes to facilitate perfusion of the intracellular compartment. Patch pipette solutions included 10 mM Na$^+$, a concentration near physiological intracellular levels and they included 500 nM recombinant FXYD1 or were FXYD1-free. Forskolin, included in the superfusate after the whole-cell configuration had been established, was used to induce an oxidant signal (Figtree et al, 2009). As shown in FIG. 2D, inclusion of FXYD1 in patch pipette solutions abolished a forskolin-induced decrease in $I_p$.

Example 3

Figure 3:
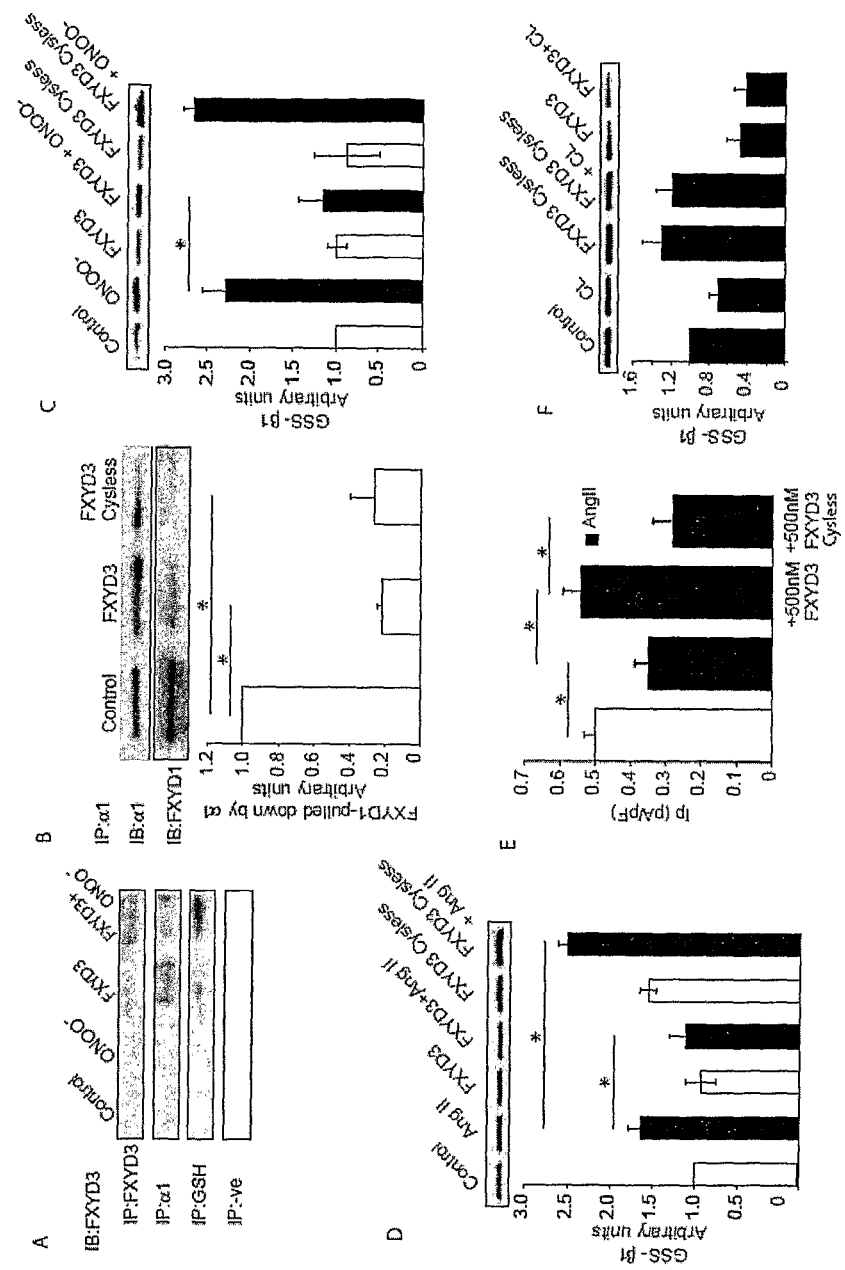
FIG. 3 illustrates the effect of recombinant FXYD3 on $Na^+$—$K^+$ pump regulation in cardiac myocytes. A. Recombinant FXYD3 protein co-immunoprecipitates with native $\alpha_1$ subunit in cardiac myocytes. FXYD3 immunoblot (IB) of FXYD3; $\alpha_1$ subunit; GSH; and non-immune control immunoprecipitate (IP) from myocytes incubated in recombinant FXYD3 (500 nM) and exposed to $ONOO^-$ or control for 10 minutes as indicated. B. Exposure of cardiac myocytes to recombinant FXYD3 decreases the co-immunoprecipitation of the native FXYD1 with the α1 subunit of the Na⁺—K⁺ pump. FXYD1 and $\alpha_1$ subunit immunoblot of $\alpha_1$ subunit immunoprecipitate from isolated cardiac myocytes exposed to either FXYD3 or the mutated cysless FXYD3. C. Effect of recombinant FXYD3 or cysless FXYD3 on ONOO⁻-induced glutathionylation of the Na⁺—K⁺ pump's $\beta_1$ subunit (GSS-β1). Myocytes were exposed to 500 nM recombinant FXYD3 (or cysless mutant) for 15 minutes prior to exposure to ONOO⁻ or control (C) for 10 minutes. D. Effect of recombinant FXYD3 or cysless FXYD3 on Ang II-induced glutathionylation of the Na⁺—K⁺ pump's 131 subunit (GSS-β1). Myocytes were exposed to 500 nM recombinant FXYD3 (or cysless mutant) for 15 minutes prior to exposure to 100 nM Ang II or control (C) for 10 minutes. E. Effect of recombinant FXYD3 or cysless FXYD3 on Ang II induced decrease in Na⁺—K⁺ pump current ($I_p$) measured in isolated cardiac myocytes. The recombinant proteins were included in the patch pipette solution at a concentration of 500 nM. The number of myocytes in each experimental group ranged from 5 to 10. F. Effect of FXYD3 or cysless FXYD3 on $\beta_3$ adrenergic agonist (CL316,243: CL)-induced decrease in β1 Na⁺—K⁺ pump subunit glutathionylation. Histograms summarise densitometry of immunoblots normalized against control (n=3 for each experiment). * indicates p<0.05 in all panels.

Recombinant FXYD3 Associates with the $\alpha_1$ Na$^+$—K$^+$ Pump Subunit and Displaces Native FXYD1 in Cardiac Myocytes Association of exogenous FXYD1 with Na$^+$—K$^+$ pump subunits may mediate the effect of FXYD1 shown in FIG. 2D. However, this is difficult to verify by immunodetection techniques since exogenous FXYD1 cannot be distinguished from native FXYD1. Conserved amino acids in all FXYD transmembrane domains, including two glycines, mediate their interaction with the Na$^+$—K$^+$ pump (Morth et al, 2007, Shinoda, 2009). An FXYD protein that is not native to cardiac myocytes was tested for association with sarcolemmal Na$^+$—K$^+$ pumps. Myocytes were exposed to recombinant 500 nMol/L human FXYD3 for 15 min. FIG. 3A shows that it co-immunoprecipitated with the native $\alpha_1$ pump subunit. We also examined if the exogenous FXYD3 could be glutathionylated. Myocytes incubated with FXYD3 for 15 min were exposed to control solutions or solutions containing ONOO$^-$. As shown in FIG. 3A, FXYD3 was glutathionylated at baseline as indicated by the detection of FXYD3 in cell lysate pulled down with an antibody to GSH. Glutathionylation was increased by ONOO$^-$. Next it was tested if exogenous FXYD3 displaces native FXYD1. FIG. 3B shows that exposure of myocytes to FXYD3 markedly decreased the co-immunoprecipitation of FXYD1 with the $\alpha_1$ Na$^+$—K$^+$ pump subunit.

Example 4

FXYD3 Reduces Glutathionylation the Na$^+$—K$^+$ Pump's Subunit in Cardiac Myocytes and Abolishes Ang II-Induced Pump Inhibition All 4 cysteines in FXYD3 were mutated to serine. Two of those cysteines are in the transmembrane segment and two are in the cytoplasmic domain. Mutation of the FXYD3 cysteines in the membrane domain does not affect association with the $\alpha_1$ Na$^+$—K$^+$ pump subunit that is mediated by the transmembrane Gly41, conserved in all FXYD proteins (Arimochi et al., 2007). FIG. 3B shows that exposure of myocytes to Cys-free FXYD3 induced a decrease in the co-immunoprecipitation of endogenous FXYD1 with the Na$^+$—K$^+$ pump $\alpha_1$ subunit, similar to that induced by wild-type FXYD3, indicating that Cys-free FXYD3 displaces native FXYD1.

To examine if FXYD3 proteins affect glutathionylation of the Na$^+$—K$^+$ pump $\beta_1$ subunit myocytes incubated with FXYD3 had no significant effect on baseline glutathionylation of the $\beta_1$ subunit As shown in FIG. 3C, incubation of myocytes with FXYD3 had no significant effect on baseline glutathionylation of the $\beta_1$ subunit. However, it abolished the increase in glutathionylation induced by ONOO$^-$. In contrast, pre-incubation with the Cysless FXYD3 mutant recombinant protein had no effect on the ONOO$^-$ induced glutathionylation. Similar experiments were performed using Ang II to induce an oxidant signal. Again, as shown in FIG. 3D, pre-incubation with FXYD3 abolished an Ang II-induced increase in glutathionylation, while the Cysless mutant protein actually increased glutathionylation, consistent with replacement of the native (Cys-containing) FXYD1 protein indicated in FIG. 3B.

In parallel functional Na$^+$—K$^+$ pump studies $I_p$ in patch clamped myocytes was measured. As shown in FIG. 3E, Ang II induced a decrease in $I_p$ that was abolished by inclusion of FXYD3 in the patch pipette solution. In contrast, Cysless FXYD3 had no effect on the Ang II induced decrease. The converse was also examined and it was found that FXYD3 affects the deglutathionylation of the $\beta_1$ Na$^+$—K$^+$ pump subunit by association with a receptor-coupled signal that induces Na$^+$—K$^+$ pump stimulation. The effect of FXYD3 on deglutathionylation of the $\beta_1$ Na$^+$—K$^+$ pump subunit was measured from baseline induced by the $\beta_3$ adrenergic receptor agonists CL316,243 (Garcia et al., 2008; Bundgaard et al, 2010). FIG. 3E shows that CL316,243 induced a decrease in glutathionylation of the $\beta_1$ subunit when myocytes had been pre-incubated with FXYD3 but an increase when myocytes had been pre-incubated with Cysless-FXYD3.

Example 5

A Specific Reactive FXYD1Cysteine Residue Modifies Glutathionylation of the $\beta_1$ Na$^+$—K$^+$ Pump Subunit and Pump Activity There are two cysteine residues in the cytoplasmic domain in FXYD with vicinal basic amino acids. One, corresponding to Cys60 (C1) in FXYD1 is partially conserved among all FXYD proteins while the other, corresponding to Cys62 (C2) is fully conserved (Cornelius and Mahmmoud, 2003) Those cysteines were examined for 'reactivity" i.e. susceptibility to glutathionylation. Cys60/Ala (FXYD1C1), Cys62/Ala (FXYD1C2) and Cys60/Ala, Cys62Ala (FXYD1C1C2) mutants were produced and examined for reactivity when expressed in *Xenopus* oocytes. FIGS. 4A and B show that wild-type FXYD1 and the FXYD1C1 mutant were readily detected in the biotin-tagged glutathionylated fraction of microsomes from oocytes injected with ONOO$^-$, but undetectable in microsomes from oocytes expressing the FXYD1C2 or FXYD1C1C2 mutants. The effect of expressing FXYD1 mutants on glutathionylation of the $\beta_1$ Na$^+$—K$^+$ pump subunit induced by exposing oocytes to ONOO$^-$ was also examined. FIGS. 4C and D show that the effect of co-expressing wild type FXYD1 to reduce glutathionylation of the $\beta_1$ pump subunit (also shown in FIG. 2A) was preserved for the FXYD1C1 mutant but eliminated for the FXYD1C2 and FXYD1C1C2 mutants.

Figure 8:
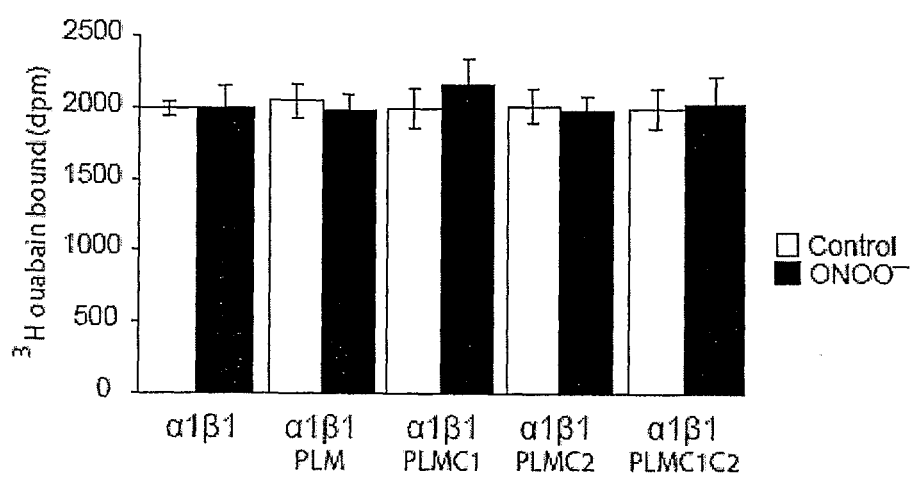
FIG. 8 illustrates the impact of mutated cysteines in FXYD1, also known as "phospholemman" (PLM) on $ONOO^-$ dependent modification of Na,K-ATPase activity. Xenopus oocytes expressing Xenopus Na,K-ATPase $\alpha_1$ and $\beta_1$ subunits alone is or together with wild type or mutated PLM (FXYD1) were injected or not with $ONOO^-$ as indicated. A. [$^3$H]ouabain binding to intact oocytes. Values obtained in non-injected oocytes were 370 dpm±27, respectively and were not subtracted. Data are means±SE of 14 oocytes from 2 different batches. B. Turnover number of Na,K-ATPase. The turnover number (charges transported/s/molecule) was calculated as the ratio between the maximal Na,K-pump current and the number of ouabain binding sites. *p<0.03 versus control.
Figure 8:
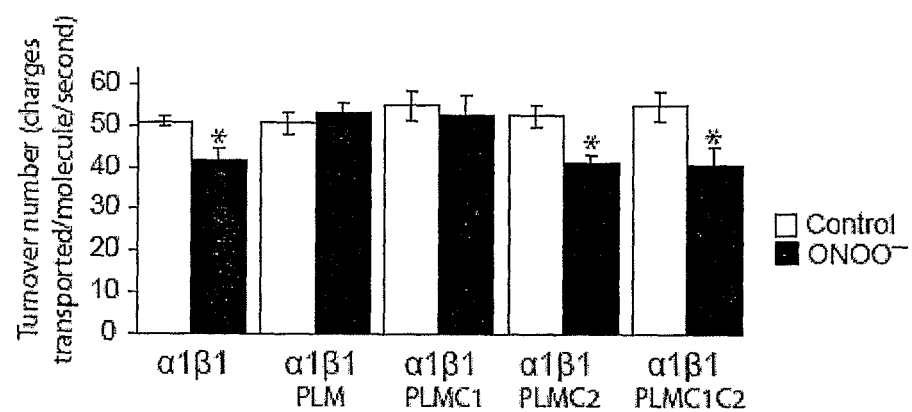
Figure 9:
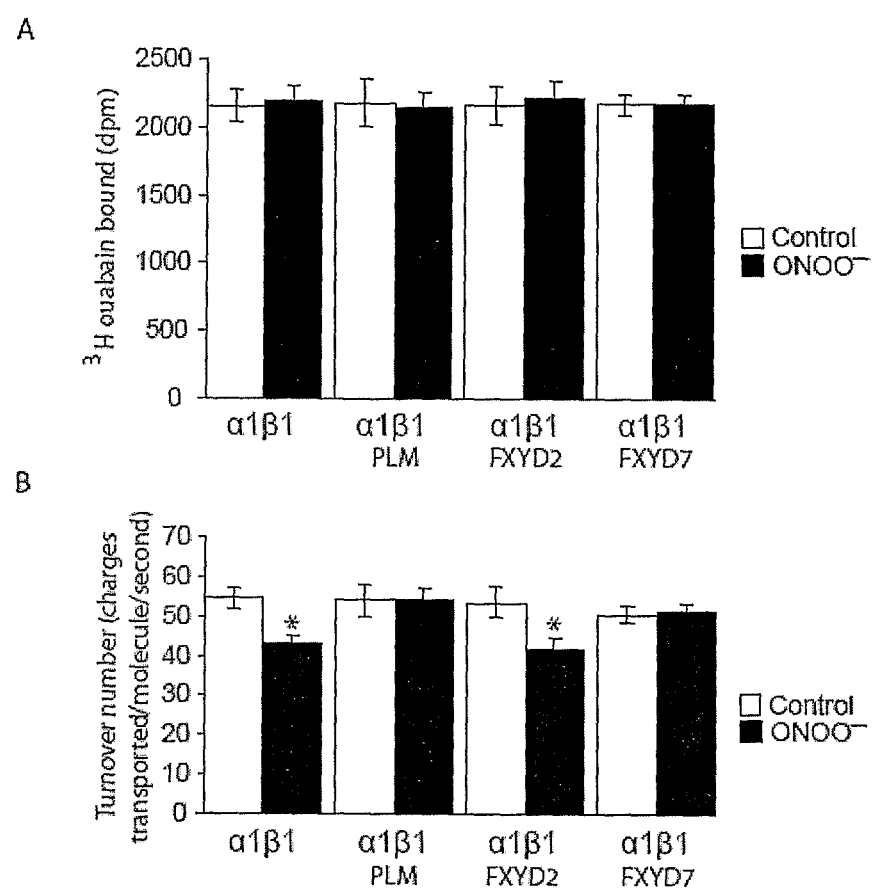
FIG. 9 illustrates the impact of different FXYD proteins on $ONOO^-$ dependent modification of Na,K-ATPase activity. Xenopus oocytes expressing Xenopus Na,K-ATPase $\alpha_1$ and $\beta_1$ subunits alone or together with wild type or mutated PLM, FXYD2 or FXYD7 were injected or not with $ONOO^-$ as indicated. A. [$^3$H]ouabain binding to intact oocytes. Values obtained in non-injected oocytes were 378 dpm±23 and 364 dpm±24 and were not subtracted. Data are means±SE of 14 oocytes from 2 different batches. B. Turnover number of Na,K-ATPase. *p<0.05 versus control.

Since glutathionylation of the $\beta_1$ subunit causes Na$^+$—K$^+$ pump inhibition the effects of FXYD mutants on $\beta_1$ subunit glutathionylation was examined and as shown in FIGS. 4C and D is reflected by effects on function. FIG. 4E shows that the effect of wild-type FXYD1 to abolish a decrease in $I_{max}$ induced by ONOO$^-$ when co-expressed with $\alpha_1/\beta_1$ subunits was preserved for the FXYD1C1 mutant but eliminated for the FXYD1C2 mutant and the FXYD1C1C2 double mutant. As previously described (Figtree et al., 2009), $^3$H-ouabain binding studies on intact oocytes indicated that ONOO$^-$ had no effect on the number of functional Na$^+$—K$^+$ pumps at the cell surface (FIG. 8), indicating that inhibition of the pump induced by ONOO$^-$ when $\alpha_1/\beta_1$ subunits were expressed alone, or co-expressed with the FXYD1C2 or FXYDC1C2 mutants, is due to a decrease in Na$^+$—K$^+$ pump turnover number (FIG. 8). We conclude that a specific, identified reactive cysteine, C62, in FXYD1 affects glutathionylation of the reactive cysteine in the $\beta_1$ subunit, Cys46 and that this effect of FXYD1 is reflected in pump function.

Example 6

Figure 5:
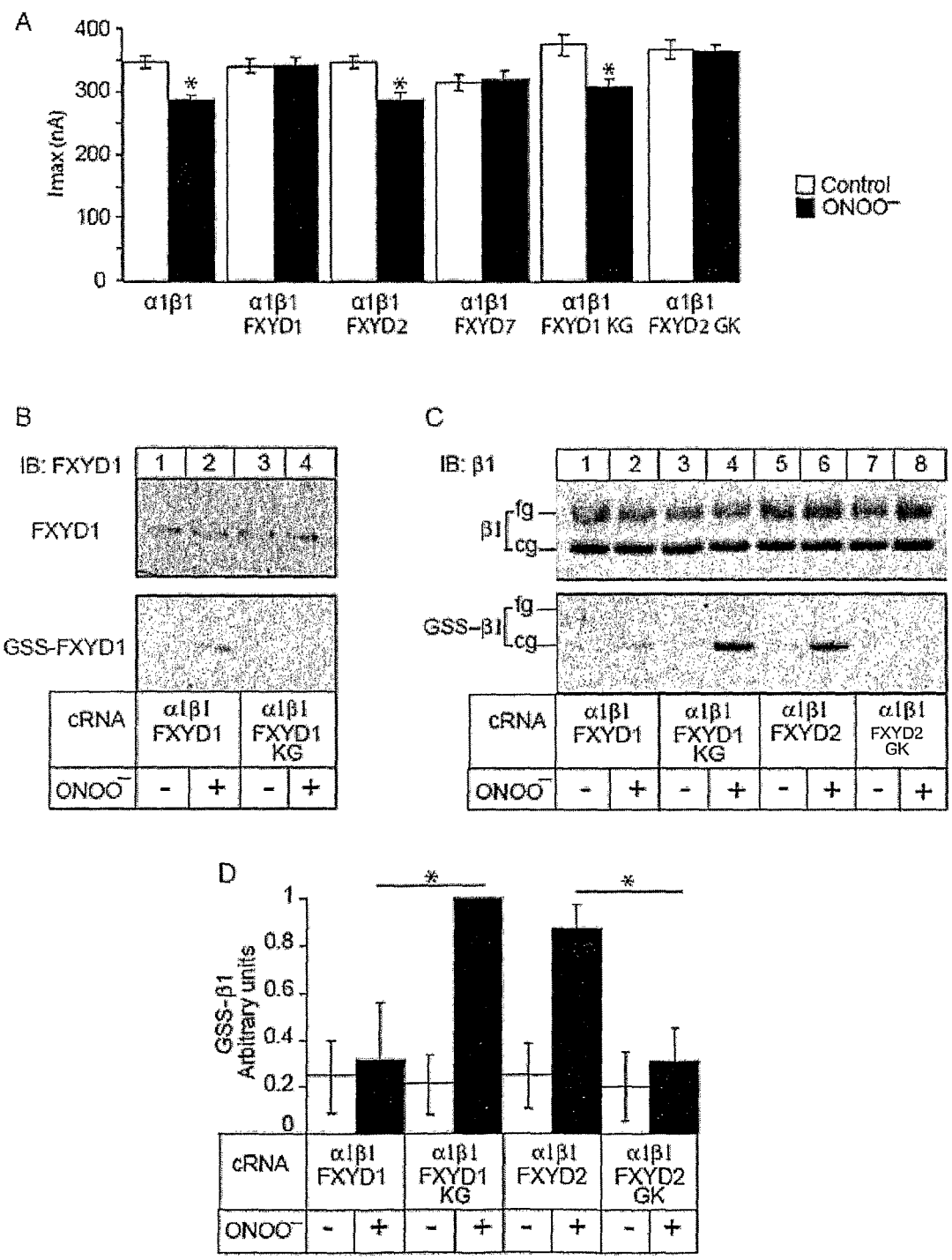
FIG. 5 illustrates amino acids surrounding candidate cysteine play a role in FXYD protein glutathionylation. *Xenopus* oocytes expressing *Xenopus* Na,K-ATPase $\alpha_1$ and β1 subunits alone or together with FXYD1, FXYD2, FXYD7, mutant FXYD1 (K63/G) or mutant FXYD2 (G49/K) were injected with biotin-GSH and ONOO— as indicated. A. Functional role of lysine adjacent to candidate cysteine in the reversion of maximal pump current inhibition. Shown are means±SE from 15 oocytes from 3 different batches. * p<0.02 versus control. Currents measured in non-injected oocytes represented 59.5 nA±4 and 51 nA±3.7 in absence and presence of ONOO⁻, respectively, and were not subtracted. Lys/Gly mutation abolishes glutathionylation of FXYD1 (B) and promotes an increase in glutathionylation of Na,K-ATPase $\beta_1$ subunit (C). Gly/Lys mutation in FXYD2 leads to a decrease in Na,K-ATPase $\beta_1$ subunit glutathionylation (C). Oocyte microsomes were either directly loaded on gels (B, C upper panels) or immunoprecipitated with streptavidin beads (B, C, lower panels) and Western blots were probed with a FXYD1 antibody (B). After stripping of the nitrocellulose membrane shown in B, the blot were probed with a Na,K-ATPase β subunit antibody (C). D. Quantification of glutathionylation of Na,K-ATPase β subunit. Shown are arbitrary units obtained by densitometric scanning of data shown in C, normalized by the total amount of proteins expressed. Data from oocytes expressing α, β and FXYD1 KG were arbitrarily set to 1. Shown are means±SE of 3 independent experiments. * p<0.05.

Basic Amino Acids Adjacent to Candidate Cysteines are Necessary for Glutathionylation of FXYD Proteins Adjacent basic amino acids, positively charged at physiological pH, are thought to facilitate formation of the disulfide bond between a protein cysteine and the negatively charged glutathione tripeptide, i.e. glutahationylation (Ghezzi, 2005). In agreement with this, Arg61 and Lys63 adjacent to the reactive Cys62 in FXYD1 are basic. However, the corresponding cysteine in FXYD2 has one adjacent basic amino acid only. FIG. 5A shows that, when overexpressed in *Xenopus* oocytes, FXYD2 had no functional effect on the decrease in $I_{max}$ induced by exposing oocytes to ONOO$^-$. The Cys62 equivalent in FXYD7 has the same vicinal amino acids as Cys62 in FXYD1, but in the reverse order (Cornelius and Mahmmoud, 2003). FIG. 5A shows that, when overexpressed in *Xenopus* oocytes, FXYD7 reproduced the ability of FXYD1 to abolish the decrease in $I_{max}$ induced by ONOO$^-$ suggesting that the charge rather than the sequence of vicinal amino acids is important for facilitating glutathionylation of reactive cysteines. The effect of mutating Lys63 in FXYD1 to the neutral Gly was examined. When overexpressed in *Xenopus* oocytes, the FXYD1 KG mutant could not reproduce the effect of wild-type FXYD1 to eliminate a decrease in $I_{max}$ induced by ONOO$^-$, glutathionylation of the mutant as shown in FIG. 5B was not detected and there was no effect of it to decrease glutathionylation of the Na$^+$—K$^+$ pump's $\beta_1$ subunit as shown in FIGS. 5C and D. In contrast, when the neutral Gly adjacent to the Cys62-equivalent in FXYD2 was mutated to the basic Lys, the FXYD2 GK mutant reproduced the effect of FXYD1 to eliminate both Na$^+$—K$^+$ pump inhibition as shown in FIG. 5A and glutathionylation of the pump's $\beta_1$ subunit as shown in FIGS. 5C and D. Antibodies against *Xenopus* FXYD2, which are efficient in immunoprecipitation (Béguin et al., 1997) but not in Western blots did not allow the glutathionylation state of FXYD2 to be established.

Example 7

Oxidative Stimuli Decrease Interaction of FXYD1 with $\alpha_1$- and Increase Interaction with $\beta_1$ Na$^+$—K$^+$ Pump Subunits Effects of FXYD proteins on the Na$^+$—K$^+$ pump are usually attributed to their association with the $\alpha$ subunits but imaging of 3D structure indicates that FXYD proteins also interact with β subunits. The effect of oxidative stimuli on alteration of the interaction of FXYD1 with $Na^+$—$K^+$ pump subunits as reflected by co-immunoprecipitation was examined. FIG. 6A shows that exposing myocytes to Ang II decreased the co-immunoprecipitation of FXYD1 with the $\alpha_1$ $Na^+$—$K^+$ pump subunits. In contrast, its co-immunoprecipitation with the $\beta_1$ subunits was increased as shown in FIG. 6B. The effect of increased oxidative stress associated with myocardial infarction affects the interaction of FXYD1 with $Na^+$—$K^+$ pump subunits was also examined. FIG. 6C shows that co-immunoprecipitation of FXYD1 with the $\alpha_1$ subunits was decreased in infarct- and border zones of the myocardium while the converse was the case for its co-immunoprecipitation with the $\beta_1$ subunits as shown in FIG. 6D.

Example 8

Figure 7:
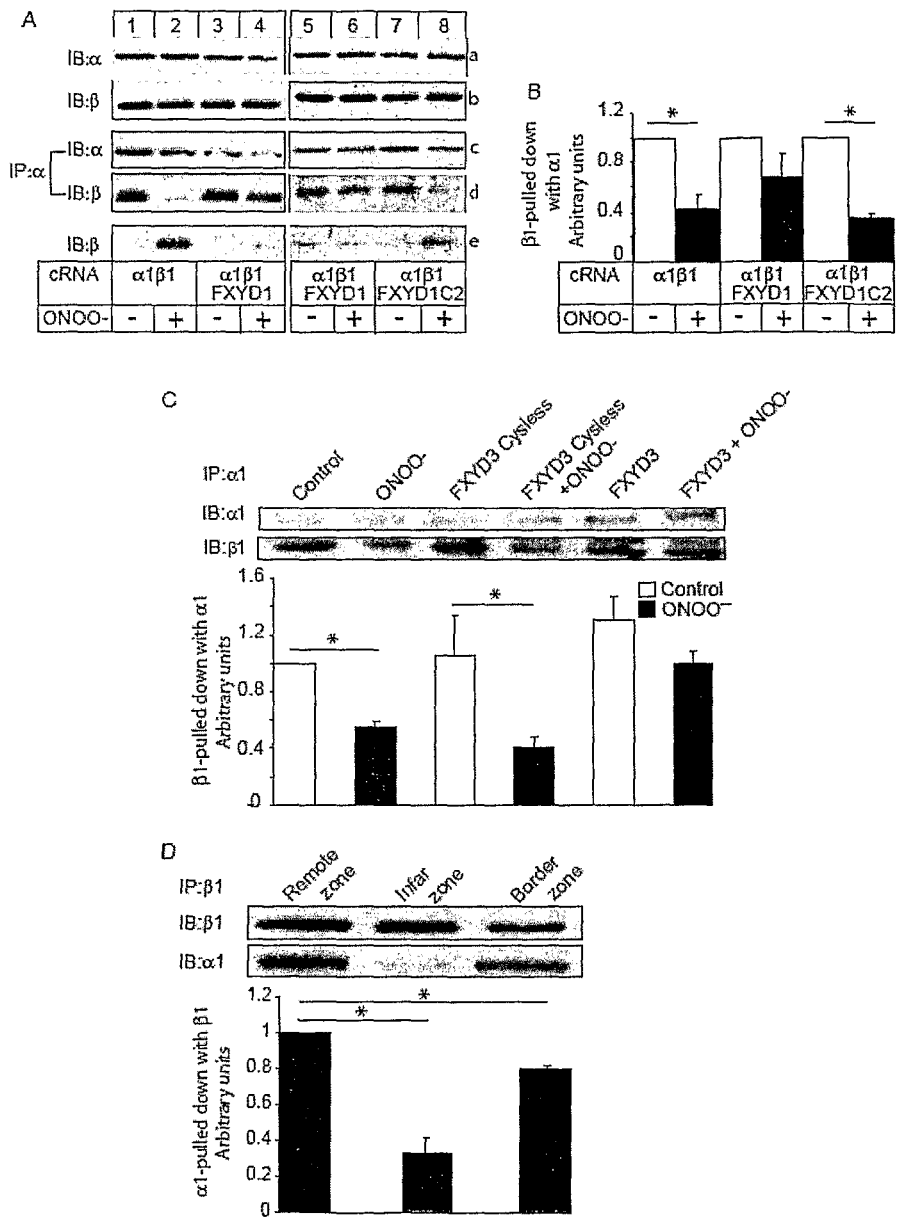
FIG. 7 illustrates that glutathionylation of Na,K-ATPase β subunit promotes a decrease in Na,K-ATPase α and β subunit association. A. $\alpha_1$/$\beta_1$ interaction in *Xenopus* oocytes. Two days after injection of *Xenopus* Na,K-ATPase α1 and β1 subunit cRNAs alone or together with FXYD1 or mutant FXYD1 (FXYD1C2) eRNAs, oocytes were injected with biotin-GSH and ONOO— as indicated. Oocyte microsomes were either directly loaded on gels (panels a, b) or immunoprecipitated with an α antibody (panels c, d) or with streptavidin beads (panels e) and Western blots were probed with a Na,K-ATPase β subunit antibody (panels b, d and e). After stripping of the nitrocellulose membrane, the blot was probed with a Na,K-ATPase α subunit antibody (panels a, c). B. Quantification of the amount of Na,K-ATPase $\beta_1$ subunit associated with Na,K-ATPase $\alpha_1$ subunit. Shown are arbitrary units obtained by densitometric scanning of data shown in A, normalized by the total amount of proteins expressed and by the amount of Na,K-ATPase α subunit immunoprecipitated. Data from oocytes expressing α and β subunits, α and β and wild type or mutant FXYD1 without ONOO— injection were arbitrarily set to 1. Shown are means±SE of 3-4 independent experiments. * p<0.05. C. Effect of recombinant FXYD3 or cysless FXYD3 on ONOO⁻-induced decrease in $\alpha_1$/$\beta_1$ subunit co-immunoprecipitation. Rabbit cardiac myocytes were exposed to ONOO⁻ as indicated. Histograms summarise densitometry of immunoblots normalized against control (n=3). * p<0.05. D. The effect of oxidant stress associated with myocardial infarction on $\alpha_1$/$\beta_1$ subunit interaction. Their co-immunoprecipitation was decreased in infarct- and peri-infarct zones of the myocardium. Histograms summarise densitometry of immunoblots normalized against control (n=3). * indicates significant difference versus control (p<0.05).

FXYD Proteins Increase Interaction Between $\alpha_1$- and $\beta_1$ $Na^+$—$K^+$ Pump Subunits Glutathionylation of the $Na^+$—$K^+$ pump's $\beta_1$ subunit decreases its co-immunoprecipitation with the $\alpha_1$ subunit (Figtree et al., 2009). Since FXYD proteins affect $\beta_1$ subunit glutathionylation (FIGS. 2 and 3), their effect on $\alpha_1/\beta_1$ subunit interaction was examined. $\alpha_1/\beta_1$ subunits were overexpressed in oocytes with or without FXYD1 or a FXYD1Cys62/Ala mutant. Panel e in FIG. 7A shows that $ONOO^-$ induced an increase in glutathionylation of the $\beta_1$ subunit when $\alpha_1/\beta_1$ subunits were overexpressed alone or co-expressed with the FXYD1 mutant. However, co-expression with wild-type FXYD1 markedly reduced $\beta_1$ subunit glutathionylation. Panel d shows that the increase in $\beta_1$ subunit glutathionylation induced by $ONOO^-$ when $\alpha_1/\beta_1$ subunits were overexpressed alone was associated with a decrease in its co-immunoprecipitation with the $\alpha_1$ subunit. This decrease was reversed when wild-type FXYD1 was co-expressed while co-expression of the FXYD1 mutant had no effect. The effect of FXYD1 and FXYD1 mutant on the co-immunoprecipitation of $\beta_1$- with $\alpha_1$ subunits is summarized in FIG. 7B. FIG. 7C shows that oxidative stress induced by ONOO— produced a decrease in $\alpha_1/\beta_1$ subunit co-immunoprecipitation also in cardiac myocytes. The recombinant Cysless FXYD3 protein had no effect on the decrease in co-immunoprecipitation induced by $ONOO^-$ but wild-type FXYD3 prevented it. FIG. 7D shows the effect of oxidant stress associated with myocardial infarction on $\alpha_1/\beta_1$ subunit interaction. Their co-immunoprecipitation was decreased in infarct- and peri-infarct zones of the myocardium.

Example 9

Methods 9.1 Studies on Mammalian Tissues and Cells

Ventricular myocytes were isolated from White New Zealand rabbits. They were used on the day of isolation only, and were stored at room temperature in Krebs-Henseleit buffer solution until used. Details of anaesthesia, excision of the heart and cell isolation techniques have been described previously.

Myocardium was obtained from a sheep model of MI (myocardial infarction) (Figtree et al, 2009). The animals were anesthetized with 20 mg/kg of thiopental sodium as induction, intubated, and ventilated with 1.5 L/min of oxygen, 2 L/min of nitrous oxide, and isoflurane (1.5% to 1.8%). Maintenance fluid was provided through peripheral venous access with Hartmann's solution (at a rate of 1 mL/kg of body weight per hour). The electrocardiograph was monitored with electrodes clipped to the extremities. MI with reperfusion was induced via a cardiac catheterisation procedure, and involved an occlusion of the left anterior descending coronary artery immediately distal to the dominant diagonal vessel, using an over-the-wire balloon catheter. The artery was occluded for 90 minutes and the balloon subsequently deflated for reperfusion. The sheep was euthanased >24 hours post induction of MI, and tissue immediately harvested for protein studies.

9.2 Immunodetection of S-Glutathionylated Proteins in Rabbit Ventricular Myocytes To detect S-glutathionylation of specific pump-related proteins, isolated myocytes were loaded with biotinylated glutathione (GSH) (500 μmmol/L; 1 hour). Biotinylated GSH ester was made by mixing 25 mmol/L sulfo-NHS-biotin with 25 mmol/L GSH ethyl ester in 50 mmol/L $NaHCO_3$ at pH 8.5 for 2 h followed by the addition of 125 mmol/L $NH_4HCO_3$ at pH 8.5 for 1 h. After incubation in biotinylated GSH ester, cells were washed 3 times with cold phosphate buffer and lysed in buffer (50 mmol/L Tris-HCl, pH 7.4, 1% Nonidet P-40, 150 mmol/L NaCl, 50 μmmol/L diethylenetriaminepentaacetic acid, 2 mmol/L phenylmethylsulfonyl fluoride) containing 10 mmol/L N-ethylmaleimide to block further thiol reactions. The biotin-tag was used to precipitate S-glutathionylated proteins using modifications of previously described methods. Approximately 0.5 mg of protein was mixed with streptavidin-sepharose beads for 1 h. The beads were washed five times with lysis buffer with 0.1% SDS, and the final precipitate was incubated for 15 min with 40 μl of elution buffer (lysis buffer+20 mmol/L DTT) to release S-glutathionylated proteins. After adding Laemmli buffer, GSS-protein pulled down by this technique was separated by gel electrophoresis, transferred to a membrane and probed with appropriate antibodies.

Separate experiments were performed using an antibody against glutathionylated protein (anti-GSH antibody). Myocytes were treated with ice-cold lysis buffer containing 150 mmol/L NaCl, 50 mmol/L Tris-HCl (pH 8.0), 1% TRITON X-100, 2 mM EDTA, and protease inhibitors (Complete EGTA-free, Roche Diagnostics). After 5 min at 4° C., the lysate was clarified by centrifugation at 16,000 g for 20 min. The supernatant (0.25-1 mg protein) was precleared and incubated with the appropriate antibody and then with protein A/G plus agarose beads. The proteins bound to the collected beads were subjected to SDS-PAGE and probed with antibodies.

The studies outlined above were performed on control myocytes, or myocytes exposed to either chemical oxidants, or oxidative stimuli activated by cell signaling. The protocols for Ang II exposure were designed to parallel previous patch-clamp studies (White et al, 2009) that were restricted in duration. The concentrations of Ang II were chosen to assure saturation binding within this time period.

9.3 Measurement of Electrogenic $Na^+$—$K^+$ Pump Current ($I_p$) in Rabbit Cardiac Myocytes Electrogenic $Na^+$—$K^+$ pump current (arising from the 3:2 $Na^+$:$K^+$ exchange ratio) was measured in single myocytes using the whole-cell patch clamp technique. Solutions were designed to minimize non-pump membrane currents. For studies using Ang II to activate oxidative signaling, wide-tipped patch pipettes (4-5 μm) were filled with solutions containing (in mmol/L): HEPES 5; MgATP 2; ethylene glycol-bis(β-aminoethyl ether)-N,N,N',N'-tetraacetic acid (EGTA) 5; potassium glutamate 70, sodium glutamate 10 and tetramethylammonium chloride (TMA-Cl) 80, and L-arginine 0.010. They were titrated to a pH of 7.20 at 35° C. with KOH. A holding potential of −40 mV was used to inactivate voltage-sensitive Na$^+$ channels. While we established the whole-cell configuration myocytes were superfused with solution containing (in mmol/L): NaCl 140; KCl 5.6; CaCl$_2$ 2.16; MgCl$_2$ 1; glucose 10; NaH$_2$PO$_4$ 0.44; N-2-hydroxyethyl piperazine-N'-2-ethene-sulphonic acid (HEPES) 10. It was titrated to a pH of 7.40 at 35° C. with NaOH. Two to three minutes after the whole cell configuration was established we switched to a superfusate that was designed to block membrane current arising from transmembrane K$^+$ and Ca$^{2+}$ gradients. It was nominally Ca$^{2+}$-free and contained and 0.2 mmol/L CdCl$_2$ and 2 mmol/L BaCl$_2$.

For studies using forskolin to activate oxidative signaling, superfusates identical to those described above were used while the whole-cell configuration was established but switched to a Na$^+$-free superfusate (NaCl replaced with NMGCl) for measurement of the ouabain-induced shift in holding current used to identify $I_p$, and the equilibrium is potential for Cl$^-$ (−14 mV), calculated from Cl$^-$ concentrations in superfusates and pipette solutions was used as the test potential. This was chosen to eliminate of cAMP-dependent Cl$^-$ current that could contaminate measurement of the relatively small pump current.

AXOCLAMP 2A and 2B voltage clamp amplifiers were used, supported by PCLAMP version 7 and Axotape version 2 (Axon Instruments, Ca, USD) to record currents. Na$^+$—K$^+$ pump current ($I_p$) was identified as the difference between holding currents, sampled at 1 Hz before and after Na$^+$—K$^+$ pump blockade with 100 μmol/L ouabain. Since pump currents are small, their identification is susceptible to contamination by currents from any source, and it is critical that only experiments with stable holding currents are included. The criteria for identification of stable currents and the ouabain-induced changes in them from samples obtained with an electronic cursor have been reported. The effect of ouabain is not reversible within the time frame stable holding currents can be reliably measured and wash-out of the effect of ouabain was not attempted. $I_p$ was normalized for membrane capacitance.

9.4 Synthesis and Purification of FXYD Proteins

Genes encoding for FXYD proteins as published in GenBank were used. The *E. coli* pMMHA fusion protein expression vector was used to direct synthesis of the fusion protein His$_9$-TrpΔLE-FXYD. The TrpΔLE fusion partner, from the Trp leader amino acid sequence, is very effective in forming inclusion bodies and is hence protected from proteolysis. The fusion protein was expressed in *E. coli* strain BL21(DE3) at levels up to 20% of total protein. After lysis of *E. coli* inclusion bodies were isolated by centrifugation and dissolved. The fusion protein was then precipitated. Intact FXYD proteins were liberated from the fusion partner using CNBr. Use of chemical cleavage eliminates difficulties such as poor specificity and enzyme inactivation often encountered with protease treatment of membrane proteins in detergents. A high degree of protein purity is achieved, as indicated by N-terminal amino acid analysis, MALDI TOF mass spectrometry and solution NMR spectroscopy (KJ Crowell et al., 2003).

9.4 *Xenopus* Oocyte Studies 9.4.1 Mutagenesis and cDNAs.

Point mutations were introduced into cDNAs of dog FXYD1 (Crambert et al., 2002) and *Xenopus* FXYD2 (Béguin et al., 1997) by the PCR-based method with mutagenic synthetic oligonucleotide primers. All products were cloned into a pSD5 vector and sequenced. cDNAs of *Xenopus* Na,K-ATPase α1 and β1, dog FXYD1 (Crambert et al., 2002), *Xenopus* FXYD2 (Béguin et al., 1997) and mouse FXYD7 (Béguin et al., 2002) were subcloned into a pSD5 vector. cRNAs were prepared by in vitro translation.

9.4.2 Expression in *Xenopus* Oocytes.

Stage V-VI oocytes were obtained from *Xenopus laevis* as described (Geering et al., 1996). Oocytes were injected with *Xenopus* α1 subunit cRNA (10 ng) and β1 subunit cRNA (1 ng) alone or together with wild type or mutant FXYD1 cRNAs (2 ng) or with wild type or mutant FXYD2 cRNAs (2 ng) or with FXYD7 cRNA (2 ng). The expression of proteins and the association of mutant FXYD proteins were verified by incubating cRNA-injected oocytes in modified Barth's solution in the presence of 1 mCi/ml [$^{35}$S] methionine (PerkinElmer Life Sciences) for 24 h. Microsomes were prepared and subjected to immunoprecipitations under nondenaturing conditions as described (Geering et al., 1996) with an antibody against the Na,K-ATPase α subunit, and proteins were resolved by SDS-PAGE and revealed by fluorography.

9.4.3 Detection of S-glutathionylation

Two days after injection, S-glutathionylation of Na$^+$—K$^+$ pump β$_1$ subunit and FXYD proteins was studied as described previously (Figtree et al., 2009). Briefly, after injection of 50 nl of 25 mM biotinylated GSH ester and incubation for 45 min at 19° C., S-glutathionylation was activated by injection of oocytes with 1 mM peroxynitrite.

After 15 min at 19° C., oocyte microsomes were prepared with buffers containing 10 mM N-ethylmaleimide. The protein content was determined by the method of Lowry. Microsomal proteins (10 μg) were subjected to SDS-PAGE or to pull down with Streptavidin-Sepharose beads (200 μg) and then transferred overnight at 40 V to to nitrocellulose membranes. Membranes were blocked with 10% nonfat dried milk in Tris-buffered saline containing 0.1% Tween-20 and incubated with *Xenopus* β$_1$ primary antibody (¹⁄₁₀₀₀), dog FXYD1 antibody (¹⁄₁₀₀₀) (Crambert et al., 2002), mouse FXYD7 (¹⁄₁₀₀₀) (Béguin et al., 2002)) or *Xenopus* FXYD2 (¹⁄₂₅₀) (Béguin et al., 1997). After binding of the primary antibody, peroxidase coupled secondary is antibodies (¹⁄₁₀,₀₀₀, Amersham Biosciences) were bound and the complex was revealed with the ECL chemiluminescence kit (Amersham Biosciences) according to the manufacturer's protocol. FXYD2 antibodies are efficient in immunoprecipitation experiments (Béguin et al., 1997) but turned out to recognize *Xenopus* FXYD2 very poorly in Western blots. In these experiments, the expression of *Xenopus* FXYD2 was confirmed by immunoprecipitation experiments on $^{35}$S-methionine labelled oocytes (data not shown).

9.5 Measurement of Maximal Na$^+$—K$^+$ Pump Current (Imax)

Electrophysiological measurements of Imax were performed 2 days after oocyte injection by using the two-electrode voltage clamp technique. Oocytes were loaded with Na$^+$ by overnight incubation in a K$^+$-free medium. The membrane potential was set at −50 mV and the Na,K-pump current was measured at room temperature as the outward current induced by the addition of 10 mM K$^+$.

For the determination of effects of peroxynitrite (ONOO$^-$) on Imax, oocytes were injected with 50 nl of 1 mM peroxynitrite 15 min before measurements.

As previously described (Figtree et al., 2009), endogenous glutathione was sufficient to see the effect of peroxynitrite on Imax.

9.6 [$^3$H]Ouabain Binding on Intact Oocytes

The total number of Na,K-ATPase expressed at the cell surface was determined by $^3$H-ouabain binding two days after injection of oocytes as previously described (Figtree et al., 2009). Briefly, oocytes were loaded with Na$^+$ in a K$^+$-free solution containing 90 mM NaCl, 1 mM CaCl$_2$, 1 mM MgCl$_2$, 10 mM Hepes, pH 7.4 for 2 h at 19° C. Oocytes were then incubated at 19° C. for 2 h in the K$^+$-free solution containing 1 mM biotinylated GSH ester. After incubation, oocytes were injected or not with 50 nl of 1 mM peroxynitrite, pH 7.4 at room temperature and incubated at room temperature for 15 min. Oocytes were then incubated in a K$^+$ free solution containing 0.3 µM [21,22-H] ouabain (Amersham, specific activity 15 Ci/mmol) and 0.7 µM cold ouabain for 30 min. Non-specific ouabain binding was determined in the presence of 300 µM cold ouabain and amounted to about 5% of total binding. Oocytes were extensively washed with a buffer containing 90 mM NaCl, 30 mM imidazole, pH 7.4, individually transferred to scintillation tubes and solubilized with 100 µl of 5% SDS. Solubilized oocytes were counted after addition of 2 ml of Scintillator 299 (Packard).

9.7 Turnover Number of Na,K-ATPase.

The turnover number was calculated as the ratio between the maximal Na,K-ATPase current (Imax) and the number of the number of pump determined by the ouabain binding.

9.8 Data analysis

Each presented immunoblot is representative of at least three separate experiments. The band densities were quantified by densitometry (Fujifilm, LAS-3000). Data are expressed as the mean±SE. Statistical comparisons were made with a Student's t test or 1 way ANOVA as appropriate. $P<0.05$ was considered to be statistically significant.

Discussion of Examples

Activity of the Na$^+$/K$^+$ pump is known to be modulated by a number of factors including cardiac glycosides, catecholamines, hormones and proteins such as FXYD.

The role of FXYD proteins in membrane function is largely attributed to their co-localization with the membrane Na$^+$—K$^+$ pump and Na$^+$—Ca$^+$ exchanger. The close association of FXYD proteins with the α- and β subunit of the Na$^+$—K$^+$ pump heterodimer is highlighted by the recent definition of the 3D structure of the α/β/FXYD complex in crystals of kidney (Morth et al., 2007) and shark rectal gland (Shinoda et al., 2009) Na$^+$—K$^+$-ATPase. Despite this close association, FXYD proteins are not an integral part of the α/β Na$^+$—K$^+$ pump heterodimer since the heterodimer alone exhibits both catalytic activity and ion-transport capacity.

FXYD1, mainly expressed in heart and skeletal muscle, is unique among FXYD proteins by being a major substrate for protein kinases A and C (Presti et al., 1985), and phosphorylation of identified amino acid residues on FXYD1 has been widely implicated in control of Na$^+$—K$^+$ pump function. However, a causal relationship between phosphorylation of these residues and effects on Na$^+$—K$^+$ pump function has not been confirmed by mutational studies. In addition, the residues are not conserved among the 6 other mammalian FXYD proteins that have no functional phosphorylation sites. While the presence of these FXYD proteins may modulate Na$^+$—K$^+$ pump function, they therefore cannot be directly implicated in protein kinase-dependent is regulation, and, if there is a generally applicable functional role of the co-localization of FXYD proteins with the Na$^+$—K$^+$ pump, it has to be independent of any direct phosphorylation of the proteins.

A mechanism that preserves the widely accepted role of protein kinases in Na$^+$—K$^+$ pump regulation but is independent of phosphorylation of FXYD proteins or of Na$^+$—K$^+$ pump subunits has now been identified. The oxidative signal of angiotensin II (Ang II)-induced, PKC-dependent activation of NADPH oxidase in cardiac myocytes, or direct exposure of exposure of myocytes to chemical oxidants induced glutathionylation of the β$_1$ subunit of the pump heterodimer (Figtree et al., 2009; White et al., 2009). Glutathionylation is a reversible oxidative modification in which the cytosolic tripeptide glutathione (GSH) forms a mixed disulfide bond with a reactive cysteine residue on a candidate protein. Glutathionylation confers a negatively charged 305 Da adduct to the protein reminiscent of phosphorylation and has been implicated in oxidative signalling. Glutathionylation is also induced by exposing Xenopus oocytes overexpressing α$_1$/β$_1$ pump subunits or Na$^+$—K$^+$ ATPase-enriched pig kidney membrane fragments to oxidants. Mutational studies identified Cys46 in the β$_1$ subunit as the reactive residue, and showed that glutathionylation was causally related to Na$^+$—K$^+$ pump inhibition (Figtree et al., 2009).

Phosphorylation of FXYD proteins, with the possible exception of FXYD1, cannot account for a role in kinase-dependent Na$^+$—K$^+$ pump regulation. However, as described herein the present inventor examined if any of their cysteine residues are "reactive", i.e. can undergo glutathionylation and if such reactive cysteines interact with the glutathionylation of the β$_1$ pump subunits and its functional equivalent, pump inhibition.

There is described herein a function of FXYD proteins never previously suspected which is that FXYD proteins modulate oxidative inhibition of the Na$^+$/K$^+$ pump by altering glutathionylation of the Na$^+$/K$^+$ pump. This discovery, contrary to existing thinking, provides a modulatory role to the members of the FXYD protein family that have no functional phosphorylation sites. That role is the reversal of Na$^+$/K$^+$ pump inhibition induced by an oxidant signal. Under physiological circumstances this signal may be hormone-receptor and NADPH oxidase-dependent. Under pathophysiological conditions the signal may arise from tissue ischaemia with or without re-perfusion, for example in myocardial infarction. FXYD proteins may also play a role in protecting cancer cells from high levels of oxidant stress.

Implications of New Role of FXYD Proteins for Disease

The role of FXYD proteins in reducing oxidative modification of the Na—K pump β$_1$ subunit as described herein has important implications for disease processes associated with increased oxidative stress. Treatments to either enhance the reducing function of FXYD proteins or abolish it may be developed.

Myocardial Infarction

Increased oxidative stress and high levels of myocyte Na$^+$ and Ca$^+$ contribute to myocardial damage and contractile abnormalities in ischemia and reperfusion. In agreement with the increase in oxidative stress, the Na$^+$—K$^+$ pump's β$_1$ subunit is glutathionylated in infarction (Figtree, 2009), and pump inhibition caused by this may contribute to the raised Na$^+$ and Ca$^{2+}$ levels. Of note, myocardial infarction is also associated with a marked increase in glutathionylation of FXYD1, (FIG. 1), a decrease of its "normal" association with the Na—K pump's α subunit and an increase in association the β$_1$ subunit (FIG. 6), consistent with a role of FXYD1 in de-glutathionylation of the β$_1$ subunit.

Treatment with antioxidants, for example vitamins A and E, have limited potential for efficacy because the cytosol contains an abundant reductant anyway. FXYD proteins may be the critical factor that allows reduction of membrane proteins, including the Na—K pump, and hence restoration of function. At the interface between the membrane and the cytosol, the reactive cysteine in FXYD proteins may provide a link to the cascade of oxidoreductases that ultimately derive their reducing power from the abundant cytosolic GSH.

Stroke

Oxidative stress has been implicated in cerebral ischaemic damage with stroke, and antioxidant strategies examined. An approach similar to that proposed for infarction, using exogenous FXYD proteins might be feasible.

Cancer

Many cancer tissues have high levels of oxidative stress and have developed increased antioxidant defences, specifically of the cytosolic oxidoreductase system.

FXYD3 is particularly well known for its possible role in cancer biology. FXYD3 (also known as Mammary tumor protein 8) is overexpressed in important cancers, including prostate, breast and pancreatic cancers. The new "membrane oxidoreductase" role we have identified suggests that the overexpression may serve to protect critical membrane proteins, including the Na—K pump, from the oxidative stress. In support of this, down-regulation of FXYD3 using gene-silencing with siRNA techniques or $Na^+$—$K^+$ pump inhibition with cardiac glycosides impairs growth of prostate cancer cells in vitro. It is also notable that observational clinical data suggests cardiac glycosides have a substantial beneficial effect on survival from breast cancer. The ion transport function as well as the $Na^+$—$K^+$ pump's role in signalling have been implicated in the possible efficacy of cardiac glycosides in cancer treatment.

Reactivity of FXYD Protein Cysteines

One, but not the other of the two best known and most comprehensively studied FXYD proteins was susceptible to glutathionylation. The susceptible protein, FXYD1 has two cysteine residues in its cytoplasmic terminal in a C1XC2 motif while FXYD2 has one candidate cysteine residue only. Mutation of C2 but not C1 abolished susceptibility to glutathionylation of FXYD1 identifying C2 as the reactive residue and also indicating that the C1XC2 motif was not critical for reactivity. Proximity of positive charges from basic amino acids are important for cysteines in a purified protein model system to react with the negatively charged GSH, and herein is described that vicinal basic amino acids are also important for glutathionylation of FXYD proteins in the cellular model described. A Gly→Lys mutation of FXYD2 to flank the candidate cysteine with basic amino acids rendered the FXYD protein reactive, and conversely, a Lys→Gly mutation removing one of the basic amino acids flanking the reactive cysteine in FXYD1 eliminated its susceptibility to glutathionylation. It should, however, be noted that C1 in FXYD1 was not reactive, despite its RC1R motif, indicating that vicinal basic amino acids promote but do not necessarily predict reactivity as recognized previously. Steric effects in the 3D structure of FXYD1 and adjacent proteins or its proximity to the membrane may also be important.

Glutathionylation and Interaction of FXYD Proteins with $Na^+$—$K^+$ Pump Subunits FXYD proteins have multiple bonds with α and β subunits of the $Na^+$—$K^+$ pump heterodimer in the transmembrane- and extracellular domain respectively (Shinoda et al., 2009). These appear to have been affected by oxidative stimuli and glutathionylation as indicted by a decrease in coimmunoprecipitation of FXYD1 with the $α_1$ subunit and an increase in its coimmunoprecipitation with the $β_1$ subunit in cardiac myocytes. This does not necessarily reflect an in situ disruption of all bonds to some $α_1$ subunit or formation of new bonds to $β_1$ subunit. Disruptions may have occurred during the experimental procedure of coimmunoprecipitation as discussed for α and β subunits previously (Figtree 2009). However, the changes in coimmunoprecipitation nevertheless suggest a change in the in situ relative strength of associations, perhaps mediated by a steric effect of the 305 Da GSH adduct.

The association of FXYD proteins with the catalytic α subunit may modify the $Na^+$—$K^+$ pump's functional properties and in principle, a change in the association induced by glutathionylation might change function. However, a critical functional role of any change in FXYD1/$α_1$ interaction is not supported in this study by the identical turnover numbers shown in FIG. 8 when $α_1/β_1$ subunits were expressed with or without FXYD1. As shown previously (Figtree, 2009) the decrease in pump function induced with oxidative stimuli, is associated with glutathionylation of the $β_1$ subunit and prevented by mutation of its only free cysteine, Cys46, indicating a causal relationship between the glutathionylation and pump inhibition. Oxidative stimuli in this study were not associated with glutathionylation of the $β_1$ subunit or inhibition of the $Na^+$—$K^+$ pump when FXYD proteins with reactive cysteines were expressed in *Xenopus* oocytes or administered exogenously to cardiac myocytes. Mutation of the reactive cysteine in the FXYD proteins eliminated these effects. These findings suggest an interaction between reactive cysteines in FXYD proteins and the $β_1$ subunit is important for function.

The FXYD proteins might prevent glutathionylation of the $β_1$ subunit and hence pump inhibition. Alternatively, they might facilitate de-glutathionylation after initial glutathionylation of the $β_1$ subunit. The spontaneous rate of de-glutathionylation is very slow but can be accelerated many orders of magnitude by oxidoreductases. Of these, glutaredoxin 1 (GR×1), mediates deglutathionylation of the mixed GSS-protein disulfide with exclusive selectivity against other protein-mixed disulfides. We have found it coimmunoprecipitates with the $Na^+$—$K^+$ pump's $β_1$ subunit in cardiac myocyte lysate and that intracellular delivery of recombinant GR×1 eliminates pump inhibition induced by an oxidant signal in voltage clamped myocytes (Figtree, 2009). The FXYD proteins may facilitate deglutathionylation of the $Na^+$—$K^+$ pump's $β_1$ subunit and perhaps other membrane proteins by providing a link to oxidoreductases, including GR×1, that are cytosolic) and hence not expected to have direct access to the membrane milieu. In the absence of any preceding oxidant stimulus, deglutathionylation of the $Na^+$—$K^+$ pump $β_1$ subunit from baseline, induced by the pump-activating $β_3$ adrenergic receptor agonist CL316,243, was blocked by Cysless- and facilitated by wild-type FXYD3 in this study, supporting a role of FXYD proteins in mediating deglutathionylation.

While it is plausible the reactive cysteine in the cytoplasmic domain, near the transmembrane segment of FXYD proteins, may interact with the strictly cytosolic cascade of oxidoreductases, the 3D structure determined for α/β/FXYD complex indicates it is not in interaction distance with the reactive Cys46 in the $β_1$ subunit in the transmembrane domain. However, the $Na^+$—$K^+$ ATPase in the crystals used to determine structure were strictly confined to the $E_2$ conformational state. The β subunit moves substantially relative to the α subunit during conformational $E_2 \leftrightarrows E_1$ conformational change of the $Na^+$—$K^+$ pump cycle (Shinoda et al., 2009), and as discussed previously there is evidence that water-filled compartments can have access to the transmembrane cysteine in the $β_1$ subunit (Figtree et al. 2009). In addition, since GSH is strictly cytosolic, the susceptibility of the $β_1$ subunit to glutathionylation indicates that Cys46 is accessible from the cytosolic compartment at some stage in the pump cycle and hence perhaps in interaction distance with reactive cysteines of FXYD proteins.

Physiological Implications

A large body of evidence indicates that the presence or absence of FXYD proteins modify functional properties and may be important for adjusting static functional pump properties according to the needs of specific tissues or cells that express them. The present study indicates they also have a broader role, integrated in a scheme of oxidative regulation that retains the firmly established roles of protein kinases in Na$^+$—K$^+$ pump regulation (White et al 2009; Figtree et al 2009) but that invokes glutathionylation rather than phosphorylation as the downstream molecular modification causing a change in function. While the scheme of pump modulation disclosed herein extends a regulatory role to most FXYD proteins, it does not include FXYD2, expressed in kidney that is not susceptible to glutathionylation nor does it is include pump heterodimers with $\beta_2$ or $\beta_3$ subunits since these relatively sparsely expressed subunits do not have a free reactive cysteine (Figtree et al 2009). Alternative mechanisms may regulate pump function where FXYD2, $\beta_2$- or $\beta_3$ subunits are expressed or a fast response to an oxidative signal may not be required.

Therapeutic Implications

A large number of pathological conditions are associated with an increase in oxidative stress and reactivity of FXYD protein cysteines may be important for their pathophysiology and treatment. Of particular relevance to this study, increased oxidative stress and high levels of myocyte Na$^+$ (and Ca$^+$ contribute to myocardial damage and contractile abnormalities in ischemia and reperfusion. In agreement with the increase in oxidative stress the Na$^+$—K$^+$ pump's $\beta_1$ subunit is glutathionylated in infarction (Figtree et al, 2009) and pump inhibition caused by this may contribute to the raised levels of Na$^+$ and Na$^+$—Ca$^{2+}$ exchange-dependent levels of Ca$^{2+}$. An abundant cellular redox buffer capacity makes it unlikely that a global change in redox status is critical in oxidant stress and treatment with antioxidants such as vitamins A and E therefore have limited potential for efficacy. The present invention shows oxidative stimuli, including myocardial infarction, are associated with glutathionylation of FXYD1. It also demonstrates the capacity of recombinant exogenous FXYD proteins to replace native FXYD1 and decrease glutathionylation of the Na$^+$—K$^+$ pump's $\beta_1$ subunit. In vivo delivery of an exogenous FXYD protein, or a smaller derivative with key feature retained, might greatly facilitate deglutathionylation of the Na$^+$—K$^+$ pump's $\beta_1$ subunit, activation of function and reversal of the adverse effects of cellular Na$^+$ and Ca$^{2+}$ overload in the acute setting of myocardial infarction.

A loss of function that depends on the reactive cysteine in FXYD proteins may have application in cancer treatment. The role of FXYD3 in facilitating deglutathionylation of the $\beta_1$ subunit may be critical for such an application. The Examples provided herein illustrate that native FXYD protein can be displaced by Cysless FXYD3 in vitro, at least in cardiac myocytes. An intravenously administered FXYD protein derivative with no reactive cysteine or critical vicinal basic amino acid residues might displace wild-type FXYD3 and eliminate its protection of Na$^+$—K$^+$ pump function from an increased oxidative load in cancer cells. Coupling of the protein to a peptide that allows selective targeting of membrane-soluble compounds to cancer cells might enhance efficacy and reduce unwanted effects in non-target tissues. Since Na$^+$—K$^+$ pump inhibition enhances irradiation damage to human tumour cell lines but not normal cell lines (Mijatovic T, Kiss R, 2007), efficacy of a therapeutic compound might also be improved when used in combination with radiotherapy or with chemotherapeutic approaches that also increase oxidative loads in cells.

REFERENCES

Arimochi, J., Ohashi-Kobayashi, A., and Maeda, M. (2007). Interaction of Mat-8 (FXYD-3) with Na$^+$/K$^+$-ATPase in colorectal cancer cells. Biol Pharm Bull 30, 648-654.

Attali, B., Latter, H., Rachamim, N., and Garty, H. (1995). A corticosteroid-induced gene expressing an "IsK-like" K+ channel activity in *Xenopus* oocytes. Proc Natl Acad Sci USA 92, 6092-6096.

Béguin, P., Crambert, G., Monnet-Tschudi, F., Uldry, M., Horisberger, J.-D., Garty, H., and Geering, K. (2002). FXYD7 is a brain-specific regulator of Na,K-ATPase {alpha}1-{beta} isozymes. EMBO J 21, 3264-3273.

Bundgaard, H, Liu C-C, Garcia A, Hamilton E J, Huang Y, Chia K K M, Hunyor S N, Figtree G A, Rasmussen H H. $\beta_3$ adrenergic stimulation of the cardiac Na$^+$—K$^+$ pump by reversal of an inhibitory oxidative modification. Circulation. "In press". Accepted Oct. 7, 2010.

Chow, D. C., Browning, C. M., and Forte, J. G. (1992). Gastric H$^+$—K$^+$-ATPase activity is inhibited by reduction of disulfide bonds in beta-subunit. Am J Physiol 263, C39-46.

Cornelius, F., and Mahmmoud, Y. A. (2003). Functional modulation of the sodium pump: the regulatory proteins "Fixit". News Physiol Sci 18, 119-124.

Crowell, K. J., Franzin, C. M., Koltay, A., Lee, S., Lucchese, A. M., Snyder, B. C., and Marassi, F. M. (2003). Expression and characterization of the FXYD ion transport regulators for NMR structural studies in lipid micelles and lipid bilayers. Biochim Biophys Acta 1645, 15-21.

Deng, V., Matagne, V., Banine, F., Frerking, M., Ohliger, P., Budden, S., Pevsner, J., Dissen, G. A., Sherman, L. S., and Ojeda, S. R. (2007). FXYD1 is an MeCP2 target gene overexpressed in the brains of Rett syndrome patients and Mecp2-null mice. Hum Mol Genet. 16, 640-650.

Figtree, G. A., Liu, C. C., Bibert, S., Hamilton, E. J., Garcia, A., White, C. N., Chia, K. K. M., Cornelius, F., Geering, K., and Rasmussen, H. H. (2009). Reversible oxidative modification: a key mechanism of Na$^+$—K$^+$ pump regulation. Circ Res 105, 185-193.

Fu, X., and Kamps, M. (1997). E2a-Pbx1 induces aberrant expression of tissue-specific and developmentally regulated genes when expressed in NIH 3T3 fibroblasts. Mol Cell Biol 17, 1503-1512.

Garcia A, Bundgaard, H, Hamilton E, Liu, C-C, Chia, KKM, Figtree G A, Rasmussen H H. $\beta_3$ adrenergic stimulation of the Na$^+$—K$^+$ pump is mediated by NO-dependent deglutathionylation of the $\beta_1$ pump subunit. Proceedings from the 12$^{th}$ International ATPase Conference, Aarhus, Denmark, 2008 (abstract).

Geering, K. (1991). The functional role of the beta-subunit in the maturation and intracellular transport of Na,K-ATPase. FEB S Lett 285, 189-193.

Geering, K. (2006). FXYD proteins: new regulators of Na—K-ATPase. Am J Physiol Renal Physiol 290, F241-250.

Ghezzi, P. (2005). Regulation of protein function by glutathionylation. Free Radic Res 39, 573-580.

Kayed, H., Kleeff, J., Kolb, A., Ketterer, K., Keleg, S., Felix, K., Giese, T., Fenzel, R., Zentgraf, H., Buchler, M. W., et al. (2006). FXYD3 is overexpressed in pancreatic ductal adenocarcinoma and influences pancreatic cancer cell growth. Int J Cancer 118, 43-54.

Meij, I. C., Koenderink, J. B., van Bokhoven, H., Assink, K. F., Groenestege, W. T., de Pont, J. J., Bindels, R. J., Monnens, L. A., van den Heuvel, L. P., and Knoers, N. V. (2000). Dominant isolated renal magnesium loss is caused by misrouting of the Na(+),K(+)-ATPase gamma-subunit. Nat Genet. 26, 265-266.

Mercer, R. W., Biemesderfer, D., Bliss, D. P., Collins, J. H., and Forbush, B. (1993). Molecular cloning and immunological characterization of the gamma-polypeptide, a small protein associated with the Na,K-ATPase. J Cell Biol 121, 579-586.

Mijatovic T. Van Quaquebeke E. Delest B. Debeir O. Darro F. Kiss R. Cardiotonic steroids on the road to anti-cancer therapy. Biochimica et Biophysica Acta. 1776(1):32-57, 2007

Morrison, B. W., Moorman, J. R., Kowdley, G. C., Kobayashi, Y. M., Jones, L. R., and Leder, P. (1995). Mat-8, a novel phospholemman-like protein expressed in human breast tumors, induces a chloride conductance in *Xenopus* oocytes. J Biol Chem 270, 2176-2182.

Morth, J. P., Pedersen, B. P., Toustrup-Jensen, M. S., Sorensen, T. L., Petersen, J., Andersen, J. P., Vilsen, B., and Nissen, P. (2007). Crystal structure of the sodium-potassium pump. Nature 450, 1043-1049.

Palmer, C. J., Scott, B. T., and Jones, L. R. (1991). Purification and complete sequence determination of the major plasma membrane substrate for cAMP-dependent protein kinase and protein kinase C in myocardium. J Biol Chem 266, 11126-11130.

Presti, C. F., Jones, L. R., and Lindemann, J. P. (1985). Isoproterenol-induced phosphorylation of a 15-kilodalton sarcolemmal protein in intact myocardium. J Biol Chem 260, 3860-3867.

Shinoda, T., Ogawa, H., Cornelius, F., and Toyoshima, C. (2009). Crystal structure of the sodium-potassium pump at 2.4 A resolution. Nature 459, 446-450.

Sweadner, K. J., and Rael, E. (2000). The FXYD gene family of small ion transport regulators or channels: cDNA sequence, protein signature sequence, and expression. Genomics 68, 41-56.

White, C. N., Figtree, G. A., Liu, C. C., Garcia, A., Hamilton, E. J., Chia, K. K., and Rasmussen, H. H. (2009). Angiotensin II inhibits the $Na^+$—$K^+$ pump via PKC dependent activation of NADPH oxidase. Am J Physiol Cell Physiol 296, C693-700.

White C N. Liu C C. Garcia A. Hamilton E J. Chia K K. Figtree G A. Rasmussen H H. (2010) Activation of cAMP-dependent signaling induces oxidative modification of the cardiac $Na+$—$K+$ pump and inhibits its activity. J Biol Chem 285, 13712-20.

Yamaguchi, F., Yamaguchi, K., Tai, Y., Sugimoto, K., and Tokuda, M. (2001). Molecular cloning and characterization of a novel phospholemman-like protein from rat hippocampus. Brain Res Mol Brain Res 86, 189-192.

---

The invention claimed is:

1. A method for treating myocardial infarction, by modulating $Na^+/K^+$ pump activity in a subject, the method comprising administering to said individual a therapeutically effective amount of an FXYD protein or a fragment or variant thereof.

2. The method according to claim 1, wherein said FXYD protein is selected from the group consisting of FXYD1, FXYD3, FXYD4 and FXYD7.

3. The method according to claim 1, wherein said fragment or variant comprises a reactive cysteine corresponding to Cys62 of FXYD1 and the transmembrane domain on FXYD 1.

4. A method for treating cancer by modulating $Na^+/K^+$ pump activity in a subject, said cancer characterized by overexpression of FXYD3, the method comprising administering to said individual a therapeutically effective amount of a loss of function FXYD protein, wherein said modulating of $Na^+/K^+$ pump activity is a decrease in pump activity.

5. The method according to claim 4, wherein said loss of function FXYD protein is an FXYD protein or fragment or variant thereof that does not comprise a reactive cysteine corresponding to Cys62 of FXYD1.

6. The method according to claim 4, wherein said loss of function FXYD protein does not comprise basic amino acids vicinal to cysteine corresponding to Cys62 of FXYD1.

7. The method according to claim 4, wherein said loss of function FXYD protein is administered in a combination treatment with one or both of radiotherapy or chemotherapy.

8. The method according to claim 4, wherein the cancer is selected from the group consisting of breast cancer, prostate cancer, pancreatic cancer and bowel cancer.

* * * * *